United States Patent
Ludwig et al.

(10) Patent No.: US 10,653,131 B2
(45) Date of Patent: *May 19, 2020

(54) PIGMENTED DECONTAMINATING GEL AND METHOD FOR DECONTAMINATING SURFACES USING SAID GEL

(71) Applicant: COMMISSARIAT À L'ÉNERGIE ATOMIQUE ET AUX ÉNERGIES ALTERNATIVES, Paris (FR)

(72) Inventors: Amélie Ludwig, Salon de Provence (FR); Frédéric Goettmann, Les Angles (FR); Fabien Frances, Rousson (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/780,632

(22) PCT Filed: Mar. 27, 2014

(86) PCT No.: PCT/EP2014/056182
§ 371 (c)(1),
(2) Date: Sep. 28, 2015

(87) PCT Pub. No.: WO2014/154817
PCT Pub. Date: Oct. 2, 2014

(65) Prior Publication Data
US 2016/0057993 A1   Mar. 3, 2016

(30) Foreign Application Priority Data

Mar. 29, 2013 (FR) .................................... 13 52906

(51) Int. Cl.
| | | |
|---|---|---|
| *A01N 25/04* | (2006.01) | |
| *A61L 2/16* | (2006.01) | |
| *G21F 9/00* | (2006.01) | |
| *A62D 3/33* | (2007.01) | |
| *A62D 3/38* | (2007.01) | |
| *C11D 3/10* | (2006.01) | |
| *C11D 3/12* | (2006.01) | |
| *C11D 3/40* | (2006.01) | |
| *C11D 17/00* | (2006.01) | |
| *A62D 101/02* | (2007.01) | |

(52) U.S. Cl.
CPC ................ *A01N 25/04* (2013.01); *A61L 2/16* (2013.01); *A62D 3/33* (2013.01); *A62D 3/38* (2013.01); *C11D 3/10* (2013.01); *C11D 3/124* (2013.01); *C11D 3/1213* (2013.01); *C11D 3/40* (2013.01); *C11D 17/003* (2013.01); *G21F 9/002* (2013.01); *A62D 2101/02* (2013.01)

(58) Field of Classification Search
CPC ................. A61L 2/0082; A61L 2/0088; A61L 2/16–186; A01N 25/02; A01N 25/04; A01N 2300/00; G21F 9/00–004
See application file for complete search history.

(56) References Cited

U.S. PATENT DOCUMENTS

| | | | |
|---|---|---|---|
| 5,670,469 A * | 9/1997 | Dingus ................... | C11D 3/18 106/31.94 |
| 6,455,751 B1 | 9/2002 | Hoffman et al. | |
| 2003/0223942 A1* | 12/2003 | Lister ..................... | C01G 49/06 424/63 |
| 2004/0175505 A1 | 9/2004 | Faure et al. | |
| 2005/0061357 A1 | 3/2005 | Steward et al. | |
| 2008/0228022 A1 | 9/2008 | Faure et al. | |
| 2013/0023713 A1 | 1/2013 | Labe et al. | |
| 2013/0171024 A1* | 7/2013 | Cuer ...................... | A01N 25/04 422/28 |

FOREIGN PATENT DOCUMENTS

| | | | | |
|---|---|---|---|---|
| FR | 2827530 A1 | 1/2003 | | |
| FR | 2891470 A1 | 4/2007 | | |
| FR | 2962046 A1 | 1/2012 | | |
| WO | 2012001046 A1 | 1/2012 | | |
| WO | WO 2012001046 A1 * | 1/2012 | ............. | A01N 25/04 |
| WO | 2014154818 A1 | 10/2014 | | |

OTHER PUBLICATIONS

Harper, B., et al., "A Comparison of Decontamination Technologies for Biological Agents on Selected Commercial Surface Materials", "Domestic Preparedness", Apr. 2001, Publisher: U.S. Army Soldier and Biological Chemical Command.
Co-pending Unpublished U.S. Appl. No. 14/647,782, filed Nov. 29, 2013.
Co-pending Unpublished U.S. Appl. No. 14/769,846, filed Nov. 8, 2013.

* cited by examiner

*Primary Examiner* — H. Sarah Park
(74) *Attorney, Agent, or Firm* — Pearne & Gordon LLP

(57) ABSTRACT

A decontamination gel is provided consisting of a colloidal solution comprising 0.1% to 30% by mass, preferably 0.1% to 25% by mass, still more preferably from 5% to 25% by mass, even more preferably 8% to 20% by mass, based on the mass of the gel, of at least one inorganic viscosifying agent; 0.1 to 10 mol/L of gel, preferably 0.5 to 10 mol/L of gel, still more preferably 1 to 10 mol/L of gel of at least one active decontamination agent; 0.01% to 10% by mass, preferably 0.1% to 5% by mass based on the mass of the gel of at least one mineral pigment; optionally, 0.1% to 2% by mass based on the mass of the gel, of at least one surfactant; optionally, 0.05% to 5% by mass, preferably 0.05% to 2% by mass, based on the mass of the gel, of at least one superabsorbent polymer; and the balance of solvent.

45 Claims, 8 Drawing Sheets

PIGMENTED DECONTAMINATING GEL AND METHOD FOR DECONTAMINATING SURFACES USING SAID GEL

CROSS-REFERENCE TO RELATED APPLICATIONS

This application is a U.S. national phase under the provisions of 35 U.S.C. § 371 of International Patent Application No. PCT/EP14/56182 filed Mar. 27, 2014, which in turn claims priority of French Patent Application No. 1352906 filed Mar. 29, 2013. The disclosures of such international patent application and French priority patent application are hereby incorporated herein by reference in their respective entireties, for all purposes.

TECHNICAL FIELD

The object of the present invention is a pigmented decontaminating gel which may be used for decontaminating surfaces.

The present invention further relates to a method for decontaminating surfaces by using this pigmented gel.

The method and the gel according to the invention allow decontamination of all kinds of surfaces such as surfaces in metal, plastic, mineral materials like glassy materials.

The method and the gel according to the invention notably apply inter alia to the decontamination of surfaces of porous materials such as cement materials like mortars and concretes; bricks; plasters; and natural stone.

The method and the gel according to the invention also allow suppression of all sorts of contaminants and notably chemical or nuclear, radioactive contaminants.

The method and the gel according to the invention may therefore be described as a NRBC (nuclear, radiological, biological, chemical) decontamination method and gel.

The technical field of the invention may thus generally be defined as being that of decontamination of surfaces with view to removing the pollutants, contaminants which are found on this surface and optionally under this surface, and the presence of which on and under these surfaces is not desired.

STATE OF THE PRIOR ART

Since a few decades, the succession of terrorist acts using chemical agents and more recently biological agents, for example the attack with sarin gas in the metro of Tokyo in 1995, and the anthrax in the letter bombs of the US Postal Service in the United States in 2001, has incited many countries to develop strategic means, so-called post-event intervention means, for efficiently reacting to the consequences of possible terrorist attacks using biological, chemical or radiological agents, and for limiting the effects of such attacks, in particular in public spaces.

Essentially of a chemical nature at the beginning of the 20$^{th}$ century, the threatening agents have evolved towards weapons of greater impact, simpler to apply and especially non-detectable before occurrence of the first symptoms on the body.

Fear is therefore today rather directed to terrorist attacks of the biological type, which are particularly contagious, but also to terrorist attacks of the chemical, nuclear or radiological type. Toxic biological species such as *Bacillus anthracis* (anthrax or charbon), the bacterium responsible for the plague *Yersinia pestis*, or further the botulinic toxin are considered as the weapons for which the probability of use is the highest.

Assuming such an event, the priority for the authorities is to limit the effects of the attack on the civil population by decontaminating and rapidly rehabilitating the exposed infrastructures, in order to avoid propagation of the toxic species through technical facilities and equipment, such as ventilation conduits and conduits for discharging waste waters, and then restore as quickly as possible the buildings to their use without any persisting risk of exposure to the toxic species for the users of these buildings.

This decontamination may pass through one of the two following steps, potentially applied in parallel:
- neutralizing, or even destroying the toxic species agent when this is possible.
- transferring the toxic species agent towards a solid or liquid phase allowing its removal.

Generally, sanitation techniques for materials contaminated by a contamination, notably a biological contamination consists of putting a liquid containing a decontamination agent, such as a biocidal agent, in contact with contaminated surfaces. The application of the decontamination solution, for example of the biocidal solution is generally achieved by spraying or by washing either coupled or not with a mechanical effect such as brushing.

An overview of these techniques is provided in documents FR-A1-2962046 and WO-A1-2012/001046 [1].

It is notably indicated therein that the decontamination products, which appear as a gel, generate solid waste and thus give the possibility of doing without the use of liquid solutions for sanitizing rooms with large surfaces and complex geometries.

These gels are generally applied by spraying them over the surface to be decontaminated.

After a period of contact of the gel with the surface to be decontaminated, equivalent to the evaporation duration of the solvent, the dry obtained waste is removed by brushing and/or suction. The major benefit of these methods is their capability of treating large surfaces and uneven geometries.

Thus, document [2] describes a gel composition containing oxidizers for chemical or biological decontamination of contaminated areas. This composition is prepared by adding thickeners or gelling agents in the form of colloids to a solution of an oxidizer in order to form a viscous colloidal gel.

The thickeners or gelling agents may be selected from among silica, alumina, aluminosilicates, mixtures of silica and alumina, and clays such as smectite.

It is indicated that these gels may be used for suppressing biological agents such as micro-organisms like bacteria, fungi, viruses and spores, or chemical agents such as neurotoxic gases.

The gels are then sprayed over the surfaces to be treated and then recovered by suction after drying.

The gelled formulations developed by the Lawrence Livermore National Laboratory under the names of L-Gel 115, and L-Gel 200 are similar to the formulations developed in document [2] and are applied with the so-called "L-Gel" method. This method seems to have some efficiency against a biological contamination such as contamination by spores of *Bacillus globigii* [3].

These gels are formulated from oxidizing acid solutions to which are added organic solvents and a silica filler. The gels are then sprayed on the surfaces to be treated and then recovered by suction after drying. Among the critical points of this method, the presence of powerful oxidizers first appears, the chemical stability of which is often very limited in time.

Moreover, in order to avoid runoffs, in particular when the gel is applied on walls or ceilings, the latter is applied in the form of very thin films with a thickness not exceeding 125 µm in document [2]. The result of this is a powdery dry waste which may cause, if the efficiency of the treatment is not complete, dissemination of the biotoxic and chemical species, such as the oxidizing compounds, into the atmosphere.

Moreover, within the scope of nuclear decontamination, gelled formulations which give the possibility of getting rid of the problems related to the powdery nature of the dry waste, and of increasing the efficiency of the method applying a gel have been the subject of documents [4] and [5].

These documents describe inorganic colloidal gels so-called "vacuumable gels", specifically formulated so as to be sprayed, and then dried with fracturation, while trapping and confining the radioactive contamination in the form of flakes which may be sucked up and stored (see FIG. 1).

The document [4] describes a gel consisting of a colloidal solution comprising an inorganic viscosifying agent, generally silica or alumina, an active treatment agent which for example is an inorganic acid or base such as soda or potash, and optionally an oxidizer having a normal oxidation-reduction potential $E_0$ greater than 1.4V in a strong acid medium, such as Ce(IV), Co(III), or Ag(II).

The document [5] describes a gel consisting of a colloidal solution comprising an organic viscosifying agent, generally silica or alumina, a surfactant, an inorganic acid or base, optionally an oxidizer having a normal oxidation-reduction potential $E_0$ greater than 1.4V in a strong acid medium such as Ce(IV), Co(III), or Ag(II).

These inorganic colloidal gels, because of the different constituents entering their composition have flow properties which allow them to be sprayed over a contaminated surface, and then their adhesion to this surface, even a vertical surface, without running off.

This thereby allows prolonged contact between the contaminant and the active decontamination agent, without altering the mechanical properties of the substrate.

Subsequent to this spraying, the gel dries, fractures and produces dry residues, called "flakes", adhering to the substrate and which are subsequently discharged by brushing or suction so as to be directly conditioned.

The decontamination methods which apply these vacuumable gels, are therefore methods for decontamination via a dry route, not generating any liquid effluent and few dry solid residues. Indeed, these dry solid residues on average only represent a fourth of the initially sprayed gel mass. Further, these methods limit the time of exposure of the operators to the radioactive contamination, because of their easy application by spraying and then suction of the dry residues, and because the presence of the operator is not required during the drying of the gel.

Documents FR-A1-2962046 and WO-A1-2012/001046 [1] relate to a "vacuumable" (aspirable) biological decontamination gel and to a method for biological decontamination of surfaces using this gel.

This gel consists of a colloidal solution comprising at least one inorganic viscosifying agent, at least one biological decontamination agent, at least one super-absorbent polymer, and at least one surfactant.

The super-absorbent polymer, such as sodium polyacrylate gives the possibility of improving the efficiency of the gel on porous materials, for example mortars.

However, practical application of these vacuumable decontamination gels, such as those described in documents [1], [4], and [5] under real conditions could be confronted with a certain number of difficulties.

Indeed, assuming the use of vacuumable decontamination gels for "post-event" treatment of civil facilities, such as railway stations or metro stations, the intervention of the operators would be made difficult mainly because of the three following factors:

stress, the intervention should be carried out rapidly without having been able to be prepared in minute detail.

wearing of pieces of individual protection equipment ("IPE"), such as NRBC Coveralls, which sometimes hamper vision and movements.

the color of the support to be decontaminated which does not necessarily contrast sharply with the colors of conventional decontamination gel formulations, i.e. what may be called the "white over white" effect.

Thus, the photograph of FIG. 4 shows the spraying of a standard non-pigmented white decontamination gel on a support to be decontaminated formed by white ceramic tiles. This photograph shows that it is difficult to distinguish the areas of the support covered with the gel, whether it is dry or wet, from the areas of the support which are not covered by the gel. In other words, it is difficult to view the wet gel, and then the dry residues obtained by drying of this gel, when the support to be decontaminated has a color, generally white, similar to that of the gel, or when the support to be decontaminated is found in a confined environment and/or in which visibility is reduced, for example a dark, poorly illuminated location. This viewing is all the more difficult since the operator wears clothing which may interfere with his/her vision such as NRBC Coveralls.

FIG. 5 represents a wall of white ceramic tiles of the Paris Metro covered with white gel. It is noticed that it is very difficult to distinguish the areas of the wall from the areas which are not covered.

It emerges from the foregoing that it is essential to facilitate and simplify the intervention of the operators responsible for decontamination under critical emergency conditions.

Therefore there exists a need for a decontamination gel which allows better viewing of the wet gel applied on a substrate, a support to be decontaminated as well as of the dry residues obtained by drying this gel on this decontaminated substrate, support.

In other words, there exists a need for a decontamination gel which gives the possibility of easily distinguishing the areas of a substrate, support, covered by the gel, whether they are dry or wet, from the areas of the substrate, support which are not covered by the gel.

This decontamination gel should ensure such an improvement in the viewing of the applied gel or of the dry residues regardless of the substrate, and notably of the color of the latter, of the contaminants to be removed, of the medium in which is found the substrate to be decontaminated, notably if this is a confined medium or with reduced visibility, of the circumstances under which decontamination is carried out for example in disaster-stricken areas and in a critical emergency situation, regardless of the decontamination clothing of the operator, notably if the latter wears NRBC Coveralls which may hamper his/her vision.

These improvements in terms of viewing the wet or dry gel should be obtained without affecting the other physico-chemical properties of the gel such as its rheology or other properties.

In particular, this gel should have all the properties of a vacuumable gel with all the advantages related to the application of such a gel in a decontamination method, which have already be discussed above.

Inter alia, the gel should have the following properties:
- easy to apply on the surface to be treated and formation of a homogenous layer;
- good adherence to the surface in order to promote optimum decontamination;
- rapid drying, for example within a period of the order of a few hours;
- forming flakes adherent to the surface to be treated, but easily recoverable by brushing and/or suction and not powdery.

This decontamination gel, for example a biological gel, should produce dry wastes, easy to remove without disseminating contaminants, for example biological contaminants, and should give the possibility of treating with the same efficiency a large variety of surfaces regardless of their shape, their geometry, their size and their nature.

There further exists a need for a decontamination gel which does not produce any chemical, mechanical or physical alteration of the treated surfaces.

The goal of the present invention is to provide a biological decontamination gel which inter alia meets the needs and requirements listed above.

The goal of the present invention is also to provide a decontamination gel which does not have the drawbacks, defects, limitations and disadvantages of the decontamination gels of the prior art and which solves the problems of decontamination gels, notably nuclear and biological gels of the prior art, notably gels, subject of documents [1], [4], and [5].

DISCUSSION OF THE INVENTION

This goal, and further other ones are achieved according to the invention with a decontamination gel, consisting of a colloidal solution comprising, preferably consisting of:
- 0.1% to 30% by mass, preferably 0.1% to 25% by mass, still preferably 5% to 25% by mass, better 8% to 20% by mass, based on the mass of the gel, of at least one inorganic viscosifying agent;
- 0.1 to 10 mol/L of gel, preferably 0.5 to 10 mol/L of gel, still preferably 1 to 10 mol/L of gel, of at least one active decontamination agent;
- 0.01% to 10% by mass, preferably 0.1% to 5% by mass, based on the mass of the gel, of at least one mineral pigment;
- optionally, 0.1% to 2% by mass based on the mass of the gel, of at least one surfactant;
- optionally, 0.05% to 5% by mass, preferably 0.05% to 2% by mass based on the mass of the gel, of at least one super-absorbent polymer;
- and the balance of solvent.

By "the balance of solvent," is meant that the solvent is always present in the colloidal solution and that the amount of solvent is an amount such that, when it is added to the amounts of the components of the colloidal solution other than the solvent (whether these components are mandatory or optional components mentioned above, or further other mentioned or not mentioned optional additional components), the total amount of all the components of the colloidal solution is 100% by mass.

The gel according to the invention is fundamentally different from the gels of the prior art, such as those of documents [1], [4], and [5] in that it contains a mineral pigment.

The decontamination gel according to the invention may thus be called a pigmented gel.

The incorporation of a mineral pigment into a decontamination gel has never been described or suggested in the prior art and notably in documents [1], [4], and [5] mentioned above.

There is no limitation as to the mineral pigment which is incorporated into the decontamination gel according to the invention.

Generally, the mineral pigment is selected from mineral pigments which are stable in the gel, notably considering the active decontamination agent which the gel contains.

By stable pigment is generally meant that the pigment does not exhibit any stable change of its color over time, upon storing the gel for a minimum period of 6 months.

There is no limitation as to the color of this pigment, which is generally the color which it will impart to the gel. This pigment may be of a black, red, blue, green, yellow, orange, violet (purple), brown color, etc. and even white.

Generally, the gel therefore has a color identical with the color of the pigment which it contains. It is, however, possible that the gel has a color which differs from the color of the pigment which it contains, for example in the case when the pigment reacts with the decontamination active agent, but this is not sought.

The pigment, notably when it is white, is generally different from the inorganic viscosifying agent.

Advantageously, the mineral pigment is selected so that it gives the gel (i.e. the gel in the wet condition as defined above, before drying) a color different from the color of a surface to be decontaminated on which the gel is applied.

Advantageously, the mineral pigment is a micronized pigment and the average size of the particles of the mineral pigment may be from 0.05 to 5 µm, preferably from 0.1 to 1 µm.

The fact that the pigment is micronized gives the possibility of avoiding modification of its flow properties and of its capability of being sprayed ("sprayability") since the pigment then has the same micrometric size which is generally that of the inorganic viscosifying agent, such as alumina aggregates.

Advantageously, the mineral pigment is selected from oxides of metal (metals) and/or metalloid(s), hydroxides of metal (metals) and/or metalloid(s), oxyhydroxides of metal (metals) and/or metalloid(s), metal (metals) ferrocyanides and ferricyanides, metal (metals) aluminates, and mixtures thereof.

Preferably, the mineral pigment is selected from iron oxides, preferably micronized, and mixtures thereof.

The iron oxides may have different colors, they may for example be yellow, red, violet (purple), orange, brown or black.

Indeed, iron oxide pigments are known to have good covering power and great resistance to acids and to bases.

For incorporation into a decontamination gel, iron oxides have the best performances in terms of stability and coloring power. Thus, an iron oxide content of 0.1%, or even 0.01% by mass is sufficient for strongly coloring the gel without modifying the properties thereof.

As this has already been indicated above, the fact that the iron oxide pigment is preferably micronized gives the possibility of avoiding modification of the flow properties and of the capability of the gel of being sprayed ("sprayability")

since the pigment then has a micrometric size, at least a size which is generally that of the inorganic viscosifying agent, such as alumina aggregates.

Micronized iron oxides are available from Rockwood® under the trade name of Ferroxide®.

Inter alia, mention may be made of Ferroxide® 212 M which is a micronized red iron oxide with an average particle size of 0.1 µm and of Ferroxide® 228 M which is a micronized red iron oxide with an average particle size of 0.5 µm.

In addition to and/or instead of iron oxides, other colored metal or metalloid oxides or hydroxides may be incorporated into the gel according to the invention, depending on the pH of the gel, mention may notably be made of vanadium oxide ($V_2O_5$) which is orange, manganese oxide ($MnO_2$) which is black, cobalt oxide which is blue or green, and rare earth oxides. However, iron oxides are preferred for the reasons specified above.

From among the oxyhydroxides, mention may be made of goethite, i.e. iron oxyhydroxide FeOOH, which is highly colored.

As an example of a metal ferrocyanide, mention may be made of Prussian Blue, i.e. ferric ferrocyanide, and as an example of an aluminate, mention may be made of cobalt blue, i.e. cobalt aluminate.

The incorporation into the gel according to the invention of a mineral pigment gives the possibility of better viewing the wet gel and then the dry residues regardless of the substrate on which is applied the gel.

Thus, FIG. 6, to be compared with FIG. 5 (white ceramic tiles covered with a white gel, without any pigment), shows a white ceramic tile, one portion of which is covered by a pigmented, colored gel according to the invention, which contains the dry and fractured Ferroxide® 212M pigment. The portion of the tile covered by the dry pigmented gel is easily distinguished from the white portion which is not covered by the gel.

Surprisingly, it was shown according to the invention that the specific coloring substance incorporated into the gel according to the invention, which is a mineral pigment, did not affect the decontaminating and physico-chemical properties of the decontamination gel according to the invention which is, like gels without any pigments, of documents [1], [4], and [5], inorganic (mineral), sprayable, vacuumable after drying and which may be used in many situations over a large range of contaminants and substrates.

In other words, it was shown according to the invention that from among all the coloring agents and pigments which might have been used for imparting color to sprayable and vacuumable decontamination gels, only mineral pigments, more particularly pigments based on oxides of metal (metals) and/or metalloid(s), hydroxides of metal (metals) and/or metalloid(s), oxyhydroxides of metal (metals) and/or metalloid(s), metal ferrocyanides and ferricyanides, metal (metals) aluminates, and mixtures thereof; and still more particularly pigments based on micronized iron oxides, were compatible with the formulation of decontamination gels, i.e. in no way affecting the required properties of these gels (see above) and the advantages which ensue.

Indeed, it was noticed that the decontaminating properties of the decontamination gels according to the invention are generally due to an aggressive formulation, for example with a very low or very high pH, and/or to the presence of oxidizers and consequently, the organic coloring agents deteriorate therein rapidly, which leads to a loss of the properties of the gel under storage conditions.

Surprisingly, only mineral pigments, more particularly pigments based on oxides, hydroxides, oxyhydroxides, ferrocyanides, ferricyanides, and aluminates, still more particularly pigments based on micronized iron oxides, provide good coloring power and good preservation of the coloration over time without however notably modifying the properties (see above) of the formulated gel.

The gels according to the invention, meet the whole of the needs and requirements mentioned above, they do not have the drawbacks, defects, limitations and disadvantages of the gels of the prior art such as those described in the documents mentioned above.

The gels according to the invention solve the problems shown by the decontamination gels of the prior art such as those described in documents [1], [4] and [5] without having the drawbacks thereof notably in terms of viewing on a substrate, areas either covered or not by the wet and dry gel, but while retaining all the known advantageous properties of these gels.

By adding mineral pigments to the standard formulation, known, of sprayable and vacuumable decontamination gels, it is possible by many aspects, to facilitate and improve their application, notably as regards their use in disaster-stricken areas, in an emergency situation in confined media or with reduced visibility, in particular for operators in NRBC Coveralls.

The presence of mineral pigments in the gel according to the invention not only ensures better viewing of the areas covered with the wet gel after spraying but also better viewing of the dry flakes on the decontaminated support.

Another additional advantage of the pigmented gels according to the invention is that it gives the possibility of easily distinguishing the dry areas, i.e. the areas covered with dry gel flakes, from the still wet gel areas.

This is possible by discoloration of the gel during drying if, of course, the pigment is not a white pigment.

Thus it is possible to visually, ensure easily and certainly that the action of the gel is completed and that the period during which it remained on the substrate was sufficient for allowing complete drying of the gel, even if this duration is random and varies depending on the weather conditions, i.e. notably on temperature, relative wetity and ventilation (FIGS. 5, 6).

The gel according to the invention may further optionally comprise a super-absorbent polymer.

The incorporation of a super-absorbent polymer in a decontamination gel and a fortiori the combination in such a gel of such a super-absorbent polymer with a decontamination agent, such as a biological decontamination agent, and with a mineral pigment have never been described in the prior art, as notably represented by the documents mentioned above.

The gel according to the invention is a colloidal solution, which means that the gel according to the invention contains inorganic, mineral solid particles of a viscosifying agent, for which the primary elementary particles have a size generally from 2 to 200 nm.

Because of the application of a generally exclusively inorganic viscosifying agent, without any organic viscosifying agent, the content of organic materials of the gel according to the invention is generally less than 4% by mass, preferably less than 2% by mass, which again is another advantage of the gels according to the invention.

These inorganic mineral solid particles play the role of a viscosifying agent in order to give the possibility to the solution, for example the aqueous solution, to gel and thus adhere to the surfaces of the part to be treated, decontaminated, regardless of their geometry, their shape, their size and wherever the contaminants to be removed are found.

Advantageously, the inorganic viscosifying agent may be selected from metal oxides such as aluminas, metalloid oxides such as silicas, metal hydroxides, metalloid hydroxides, metal oxyhydroxides, metalloid oxyhydroxides, aluminosilicates, clays such as smectite, and mixtures thereof.

In particular, the inorganic viscosifying agent may be selected from among aluminas ($Al_2O_3$) and silicas ($SiO_2$).

The inorganic viscosifying agent may only comprise a single silica or alumina or a mixture of the latter, i.e. a mixture of two different silicas or more ($SiO_2/SiO_2$ mixture), a mixture of two different aluminas or more ($Al_2O_3/Al_2O_3$ mixture), or further a mixture of one or several silica(s) with one or several alumina(s) ($SiO_2/Al_2O_3$ mixture).

Advantageously, the inorganic viscosifying agent may be selected from pyrogenated silicas, precipitated silicas, hydrophilic silicas, hydrophobic silicas, acid silicas, basic silicas like Tixosil® 73 silica, marketed by Rhodia, and mixtures thereof.

From among acid silicas, mention may notably be made of pyrogenated silicas or silica fumes "Cab-O-Sil"® M5, H5 or EH5, marketed by CABOT, and pyrogenated silicas marketed by EVONIK INDUSTRIES under the name of AEROSIL®.

Among these pyrogenated silicas, the silica AEROSIL® 380 with a specific surface area of 380 $m^2/g$ will further be preferred, which provides maximum viscosifying properties for a minimum mineral load.

The silica used may also be a so-called precipitated silica for example obtained via a wet route by mixing a solution of sodium silicate and of an acid. The preferred precipitated silicas are marketed by EVONIK INDUSTRIES under the name of SIPERNAT® 22 LS and FK 310 or further by RHODIA under the name of TIXOSIL® 331, the latter is a precipitated silica, the average specific surface area of which is comprised between 170 and 200 $m^2/g$.

Advantageously, the inorganic viscosifying agent consists of a mixture of precipitated silica and of pyrogenated silica.

The alumina may be selected from calcined aluminas, milled calcined aluminas, and mixtures thereof.

As an example, mention may be made of the product sold by EVONIK INDUSTRIES under the trade name of "Aeroxide Alumina C" which is fine pyrogenated alumina.

Advantageously, according to the invention, the viscosifying agent consists of one or several alumina(s) generally representing from 5% to 30% by mass based on the mass of the gel.

In this case, the alumina is preferably at a concentration from 8% to 17% by mass based on the total mass of the gel in order to ensure drying of the gel at a temperature comprised between 20° C. and 50° C. and at a relative wetity comprised between 20% and 60% on average over 30 minutes to 5 hours.

The nature of the mineral viscosifying agent, notably when it consists of one or several aluminas, unexpectedly influences the drying of the gel according to the invention and the grain size of the obtained residue.

Indeed, the dry gel appears as particles with a controlled size, more specifically millimetric solid flakes, the size of which is generally from 1 to 10 mm, preferably from 2 to 5 mm notably thanks to the aforementioned compositions of the present invention, in particular when the viscosifying agent consists of one or several alumina(s).

Let us specify that the size of the particles generally corresponds to their largest dimension.

In other words, the mineral solid particles of the gel according to the invention, for example of the silica or alumina type, in addition to their role of viscosifying agent, also play a fundamental role during the drying of the gel since they ensure fracturation of the gel in order to result in a dry waste in the form of flakes.

The gel according to the invention contains an active decontamination agent. This active decontamination agent may be any active decontamination agent allowing removal of a contaminant regardless of the nature of this contaminant: regardless of whether this contaminant is chemical, biological or further nuclear, radioactive, in other words, this decontamination agent may be any "NRBC" (nuclear, biological, radiological, chemical) decontamination agent, or regardless of whether this contaminant is organic or mineral, liquid or solid; or regardless of the shape of this contaminant: of whether this contaminant is in a massive or particulate form, contained in a surface layer of the material of the part, in the form of a film or contained in a film, for example a film of fats at the surface of the part, in the form of a layer or contained in a layer, for example a layer of paint at the surface of the part, or quite simply deposited on the surface of the part.

Depending on the nature of the contamination, the modes of action of the gels are different: erosion of the supporting material containing the contamination, solubilization of the contaminating film, for example of fats, or for example of a paint cover, or further inactivation in situ of the chemical or biological contaminants in the case of pathogenic species (anthrax).

The gel according to the invention may thus contain a biological or chemical or further nuclear, radioactive decontamination active agent; the active decontamination agent may also be a degreasing, stripping agent. Certain active decontamination agents may simultaneously play several decontamination functions.

By biological decontamination agent which may also be described as a biocidal agent, is meant any agent, which, when it is put into contact with a biological species and notably a toxic biological species is capable of inactivating or destroying the latter.

By biological species, is meant any type of microorganism such as bacteria, fungi, yeasts, viruses, toxins, spores, notably spores of *Bacillus anthracis*, prions, and protozoa.

The biological species which are removed (eliminated), destroyed, inactivated by the gel according to the invention are essentially biotoxic species such as pathogenic spores such as for example the spores of *Bacillus anthracis*, toxins such as for example botulinic toxin or ricin, bacteria like the bacteria *Yersinia pestis* and viruses like the virus of vaccine or viruses of hemorrhagic fevers for example of the Ebola type.

By chemical decontamination agent, is meant any agent which, when it is put into contact with a chemical species and notably a toxic chemical species, is able to destroy or inactivate the latter.

The chemical species which are removed by the gel according to the invention are notably toxic chemical species such as toxic gases, in particular neurotoxic or blistering gases.

These toxic gases are notably organophosphorus compounds, among which mention may be made of Sarin or GB agent, VX, Tabun or GA agent, Soman, Cyclosarin, diisopropyl fluorophosphonate (DFP), Amiton or VG agent, Parathion. Other toxic gases are mustard gas or H agent or HD agent, Lewisite or L agent, T agent.

The nuclear, radioactive species which may be removed with the gel according to the invention may for example be selected from metal oxides and hydroxides notably as solid precipitates.

It should be noted that in the case of radioactive species, reference is not made to destruction or inactivation but only to removal (elimination) of the contamination by dissolving radiating deposits or by corrosion of the contamination-supporting materials. Therefore there is truly a transfer of nuclear contamination towards the dry gel flakes.

The active decontamination agent, for example the active biological or chemical decontamination agent, may be selected from bases such as sodium hydroxide, potassium hydroxide, and mixtures thereof; acids such as nitric acid, phosphoric acid, hydrochloric acid, sulfuric acid, hydrogenoxalates like sodium hydrogenoxalate and mixtures thereof; oxidizers such as peroxides, permanganates, persulfates, ozone, hypochlorites such as sodium hypochlorite, cerium IV salts and mixtures thereof; quaternary ammonium salts such as hexacetylpyridinium salts, like hexacetylpyridinium chloride; reducing agents; and mixtures thereof.

Certain active decontamination agents may be classified among several of the categories mentioned above.

Thus, nitric acid is an acid but also an oxidizer.

The active decontamination agent, such as a biocidal agent, is generally used at a concentration from 0.5 to 10 mol/L of gel, preferably from 1 to 10 mol/L, and still preferably from 3 to 6 mol/L of gel in order to guarantee a decontamination power, for example a power for inhibiting biological, notably biotoxic species, compatible with the drying period of the gel, and for ensuring e.g. drying of the gel at a temperature comprised between 20° C. and 50° C. and at a relative wetity comprised between 20% and 60% on average within 30 minutes to 5 hours.

In order to attain complete efficiency, including under the most unfavorable temperature and wetity conditions towards the drying period, the formulation of the gel of the present invention supports different concentrations of active agent. It may be noted actually, that the increase in the concentration of a decontamination agent, more particularly of an acid or basic decontamination agent, considerably increases the drying period of the gel and therefore the efficiency of the method. In order to take into account erosion kinetics of the materials and inhibition kinetics of the contaminating species, notably biotoxic species, the active decontamination agent, notably the biological decontamination agent, will preferably be present in the gel at a concentration comprised between 3 and 6 mol/L in order to attain maximum efficiency of the method.

The active decontamination agent may be an acid or a mixture of acids. These acids are generally selected from among mineral acids such as hydrochloric acid, nitric acid, sulfuric acid and phosphoric acid.

A more preferred decontaminating agent, notably a biological decontaminating agent, is nitric acid.

Indeed, it proved to be totally surprising that nitric acid destroyed, inactivated, biological species notably biotoxic species.

In particular, it was surprisingly shown that nitric acid ensured destruction, inactivation of spores such as the spores of *Bacillus thuringiensis* which are particularly resistant species.

The acid or the acids is (are) preferably present at a concentration from 0.5 to 10 mol/L, still preferably from 1 to 10 mol/L, better from 3 to 6 mol/L for ensuring drying of the gel generally at a temperature comprised between 20° C. and 50° C. and at a relative wetity comprised between 20% and 60% on average within 30 minutes to 5 hours.

For this type of acid gel, the inorganic viscosifying agent is preferably silica or a mixture of silicas.

Or else, the active decontamination agent, for example the active biological decontamination agent may be a base, preferably a mineral base, preferably selected from soda, potash and mixtures thereof.

In the case of such a formulation of a basic gel, the gel according to the invention in addition to the decontamination action, has a degreasing action.

As this has already been mentioned above, in order to attain complete efficiency, including under the most unfavorable weather conditions toward the drying period of the gel, the gel according to the invention may have a large range of concentrations of basic decontamination agent(s).

Indeed, the increase in the concentration of basic decontamination agent like NaOH or KOH, generally playing the role of a biocidal agent, gives the possibility of considerably increasing the inhibition rates of biological species, as this was demonstrated for spores of *Bacillus thuringiensis.*

The base is advantageously present at a concentration of less than 10 mol/L, preferably between 0.5 and 7 mol/L, still preferably between 1 and 5 mol/L, better between 3 and 6 mol/L, in order to ensure drying of the gel at a temperature comprised between 20° C. and 50° C. and at a relative wetity comprised between 20% and 60% on average within 30 minutes to 5 hours.

For this type of alkaline, basic gel, the inorganic viscosifying agent is preferably an alumina or a mixture of aluminas.

In order to reach maximum efficiency over a large range of materials while guaranteeing innocuousness of the treatment, the decontamination agent in particular when this is a biological decontamination agent, is preferably sodium hydroxide or potassium hydroxide.

In the case of the treatment of a cement matrix, the basic pH of the gel, which is induced by the use of soda or potash, gives the possibility of avoiding acid-base reactions, between the material to be decontaminated and the gel, which are detrimental to the integrity of the gel on the surface and therefore to the efficiency of the method.

The hygroscopic nature of sodium hydroxide or potassium hydroxide is also a considerable asset for slowing down the gel drying phenomenon. The contact time between the gel according to the invention, containing for example a biocidal solution, and the biological contamination, is then considerably increased.

Indeed, the competition between the process for evaporating the active phase and that of uptaking water by the sodium hydroxide or potassium hydroxide crystals favorably modifies the kinetics for drying the gel.

For example considering the kinetics for inhibiting the spores and the drying periods of the gels versus temperature, the active decontamination agent, notably when this is a biocidal agent will be preferably sodium hydroxide at a concentration comprised between 1 and 5 mol/L.

The gel according to the invention may further contain, optionally a super-absorbent polymer.

By "super-absorbent polymer" also designated as "PSA", is generally meant a polymer capable, in the dry condition, of spontaneously absorbing at least 10 times, preferably at least 20 times its weight of aqueous liquid, in particular of water and notably of distilled water.

Certain "PSAs" may absorb up to a 1,000 times their weight of liquid and even more.

Such super-absorbent polymers are notably described in the text book "*Absorbent Polymer Technology, Studies in Polymer Science* 8" of L. BRANNON-PAPPAS and R. HARLAND, Elsevier editions, 1990, to which reference may be made.

By spontaneous absorption, is meant an absorption period ranging up to about one hour.

The super-absorbent polymer may have a water absorption capacity ranging from 10 to 2,000 times its own weight, preferably from 20 to 2,000 times its own weight (i.e. 20 g to 2,000 g of water absorbed per gram of absorbent polymer), still preferably from 30 to 1,500 times, and in particular from 50 to 1,000 times.

These water absorption characteristics are understood under normal conditions of temperature (25° C.) and of pressure (760 mmHg or 100,000 Pa) and for distilled water.

The PSA optionally contained in the decontamination gel according to the invention may be selected from sodium poly(meth)acrylates, starches grafted with a (meth)acrylic polymer, hydrolyzed starches grafted with a (meth)acrylic polymer; polymers based on starch, gum, and cellulose derivative; and mixtures thereof.

More specifically, the PSA which may optionally be used in the gel according to the invention may for example be selected from among:

polymers resulting from polymerization with partial cross-linking of water-soluble monomers with ethylenic unsaturation, such as acrylic, methacrylic polymers (notably stemming from polymerization of acrylic and/or methacrylic acid and/or from acrylate and/or methacrylate monomers) or vinyl polymers, in particular cross-linked and neutralized poly(meth)acrylates, notably as a gel; and the salts notably the alkaline salts such as sodium or potassium salts of these polymers;

starches grafted with polyacrylates;

acrylamide/acrylic acid copolymers, notably as sodium or potassium salts;

starches grafted with acrylamide/acrylic acid, notably as sodium or potassium salts;

sodium or potassium salts of carboxymethylcellulose;

salts, notably alkaline salts of cross-linked polyaspartic acids;

salts, notably alkaline salts, of cross-linked polyglutamic acids.

In particular, it is possible to use as a "PSA" a compound selected from among:

cross-linked sodium or potassium polyacrylates marketed under the names of SALSORB CL 10, SALSORB CL 20, FSA type 101, FSA type 102 (Allied Colloids); ARASORB S-310 (Arakawa Chemical); ASAP 2000, Aridall 1460 (Chemdal); KI-GEL 201-K (Siber Hegner); AQUALIC CA W3, AQUALIC CA W7, AQUALIC CA W10; (Nippon Shokuba); AQUA KEEP D 50, AQUA KEEP D 60, AQUA KEEP D 65, AQUA KEEP S 30, AQUA KEEP S 35, AQUA KEEP S 45, AQUA KEEP AI M1, AQUA KEEP AI M3, AQUA KEEP HP 200, NORSOCRYL S 35, NORSOCRYL FX 007 (Arkema); AQUA KEEP 10SH-NF, AQUA KEEP J-550 (Kobo); LUQUASORB CF, LUQUASORB MA 1110, LUQUASORB MR 1600, HYSORB C3746-5 (BASF); COVAGEL (Sensient technologies), SAN-WET IM-5000D (Hoechst Celanese);

starch-grafted polyacrylates marketed under the names of SANWET IM-100, SANWET IM-3900, SANWET IM-50005 (Hoechst);

acrylamide/acrylic acid copolymers grafted with starch as a sodium or potassium salt marketed under the names of WATERLOCK A-100, WATERLOCK A-200, WATERLOCK C-200, WATERLOCK D-200, WATERLOCK B-204 (Grain Processing Corporation);

acrylamide/acrylic acid copolymers as a sodium salt, marketed under the name of WATERLOCK G-400 (Grain Processing Corporation);

carboxymethylcellulose marketed under the name of AQUASORB A250 (Aqualon);

cross-linked sodium polyglutamate marketed under the name of GELPROTEIN (Idemitsu Technofine).

Super-absorbent polymers, in particular super-absorbent polymers (polyelectrolytes) which contain alkaline ions such as sodium or potassium ions, for example of the sodium or potassium poly (meth)acrylate type, give many properties to decontamination gels according to the invention.

First of all, they influence the flow properties of the product, notably its flow threshold. In terms of application of the method, the benefit of super-absorbent polymers is to guarantee perfect adherence of the gel on the treated materials, notably on vertical surfaces and overhanging surfaces when the sprayed gel thickness is greater than 1 mm.

Within the scope of a decontamination method, notably a biological decontamination method by a gel, the super-absorbent polymer is particularly of interest since it absorbs by a hydrogen bond, a portion of the solution, for example of the biocidal solution, contained in the gel. As the number of hydrogen bonds formed between the solution, for example the biocidal solution, of the gel and the super-absorbent polymer such as sodium polyacrylate depend on the saline load, absorption/desorption phenomena appear when the saline load of the decontamination gel is modified.

This mechanism is then of particular interest when the question is to decontaminate mineral and porous materials such as cement matrices for example.

Indeed, in contact with the material, the saline load of the gel increases because of the presence of mineral particles, very often based on calcium. Within the super-absorbent polymer such as sodium polyacrylate, substitution of the counter-ion $Na^+$ with $Ca^{2+}$ from calcium instantaneously generates a phenomenon of de-salting of the solution, for example of the biocidal solution, because of greater steric hindrance of the calcium ion.

The amount of solution, for example of biocidal solution, released by the super-absorbent polymer such as sodium polyacrylate may then instantaneously diffuse into the porosity of the material and penetrate it in depth.

The diffusion phenomenon of the decontamination agent, for example of the biocidal agent, towards the core of the material is much more limited in the case of a gel not containing any super-absorbent.

Addition of super-absorbent polymer to the gel according to the invention therefore gives the possibility of significantly increasing the efficiency of the gel and of the method according to the invention in the presence of porous materials contaminated in depth over a thickness from one to several millimeters, for example up to 2, 5, 10, 20 or even 100 mm.

The super-absorbent polymer may preferably be selected from the Aquakeep® or Norsocryl® ranges marketed by ARKEMA.

The gel may optionally also contain a surfactant or a mixture of surfactants, preferably selected from the family of non-ionic surfactants such as block, sequenced, copolymers, like the block copolymers of ethylene oxide and propylene oxide, and ethoxylated fatty acids; and mixtures thereof.

For this type of gel, the surfactants are preferably block copolymers marketed by BASF under the name of PLURONIC®.

The Pluronics® are block copolymers of ethylene oxide and propylene oxide.

These surfactants influence the flow properties of the gel, notably the thixotropic nature of the product and its recovery time and avoid the occurrence of runoff.

Moreover the surfactants give the possibility of controlling the adhesion of the dry waste, and of controlling the size of the dry residue flakes in order to guarantee the non-powdery nature of the waste.

The solvent according to the invention is generally selected from among water, organic solvents, and mixtures thereof.

A preferred solvent is water, and in this case, the solvent consists of water, comprises 100% of water.

The invention further relates to a method for decontaminating at least one surface of a substrate made of a solid material, said surface being contaminated by at least one contaminating species found on said surface and optionally under said surface in the depth of the substrate, wherein at least one cycle is carried out comprising the following successive steps:

a) the gel according to the invention as described above is applied on said surface;

b) the gel is maintained on the surface at least for a sufficient time (duration) so that the gel destroys and/or inactivates and/or absorbs the contaminating species, and so that the gel dries and forms a dry and solid residue containing said contaminating species;

c) the dry and solid residue containing said contaminating species is removed (eliminated).

It should be noted, that in the case of a non-porous surface, the contamination, for example the biological contamination, which is inactivated, is recovered by the dry gel flakes.

On the other hand, in the case of deep contamination, as this is the case in porous materials such as cement matrices, the dry gel will only contain the surface contamination residue.

The deep, internal contamination inactivated in situ following the action of the super-absorbent polymer which is then advantageously incorporated into the gel, will remain in the core of the material, substrate.

Advantageously, the mineral pigment contained in the gel is selected so that it gives the gel a color different from the color of the surface to be decontaminated on which the gel is applied.

The solid substrate may be a porous substrate, preferably a porous mineral substrate and the gel according to the invention then advantageously contains a super-absorbent polymer.

However, the efficiency of the gel and of the method according to the invention is quite as good in the presence of a non-porous and/or non-mineral surface.

Advantageously, the substrate is made of at least one solid material selected from metals and metal alloys such as stainless steel, painted steels, aluminium, and lead; polymers such as plastic materials or rubbers like poly(vinyl chloride)s or PVC, polypropylenes or PP, polyethylenes or PE notably high density polyethylenes or HDPE, poly(methyl methacrylate)s or PMMA, poly(vinylidene fluoride)s or PVDF, polycarbonates or PC; glasses; cements and cement materials; mortars and concretes; plasters; bricks; natural or artificial stone; ceramics.

Advantageously, the contaminating species is selected from the chemical, biological, nuclear or radioactive contaminating species already listed above and notably from among the toxic biological species already listed above.

Advantageously, the gel is applied on the surface to be decontaminated in an amount from 100 g to 2,000 g of gel per $m^2$ of surface, preferably from 500 to 1,500 g of gel per $m^2$ of surface, still preferably from 600 to 1,000 g of gel per $m^2$ of surface, which generally corresponds to a thickness of deposited gel on the surface comprised between 0.5 mm and 2 mm.

Advantageously, the gel is applied on the solid surface by spraying, with a brush or with a trowel.

Advantageously (during step b)), drying is achieved at a temperature from 1° C. to 50° C., preferably from 15° C. to 25° C., and under a relative wetity from 20% to 80%, preferably from 20% to 70%.

Advantageously, the gel is maintained on the surface for a period from 2 to 72 hours, preferably from 2 to 48 hours, still preferably from 3 to 24 hours.

Advantageously, the gel is maintained on the surface until it exhibits a reduction in its visible and ultraviolet light absorbance, for example a discoloration. This reduction of the absorbance generally indicates that the drying has been completed, and that decontamination is complete.

By reduction in the absorbance, is generally meant that the absorbance of the dry gel (of the flakes) decreases by 30% to 99% relatively to the absorbance which the wet gel initially has upon applying the gel on the surface to be decontaminated.

Advantageously, the dry and solid residue appears in the form of particles, for example flakes, with a size from 1 to 10 mm, preferably from 2 to 5 mm.

Advantageously, the dry and solid residue is removed (eliminated) from the solid surface by brushing and/or suction.

Advantageously, the cycle described above may be repeated for example from 1 to 10 times by using the same gel during all the cycles or by using different gels during one or several cycle(s).

Advantageously, during step b), the gel, before complete drying, is re-wetted with a solution of a decontamination agent, preferably with a solution of the active decontamination agent of the gel applied during step a) in the solvent of this gel which then generally avoids repeating the application of the gel on the surface and causes savings in reagent and a limited amount of waste. This re-wetting operation may be for example repeated from 1 to 10 times.

The method according to the invention has all the advantageous properties inherent to the decontamination gel which it applies and which have already been widely discussed above.

As a summary, the method and gel according to the invention have inter alia further to the advantageous properties specifically due to the mineral pigment contained in the gel, the other following advantageous properties:

application of the gel by spraying,
adherence to the walls,
obtaining maximum decontamination efficiency at the end of the drying phase of the gel, including in a situation of penetrating contamination notably in the case of porous surfaces.

Generally, it is ensured that the drying period is greater than or equal to the time required for inactivation. In the case of deep inactivation, one generally resorts to re-wetting.

the treatment of a very wide range of materials, the absence of any mechanical or physical alteration of the materials at the end of the treatment, the application of the method under variable weather conditions, reduction in the waste volume, the dry waste is easily recovered.

Other features and advantages of the invention will become better apparent upon reading the detailed description which follows, this description being made as an illustration and not as a limitation, in connection with the appended drawings.

SHORT DESCRIPTION OF THE DRAWINGS

The wavelength (in nm) is plotted in abscissas, and the absorbance is plotted in ordinates.

Figure 8:
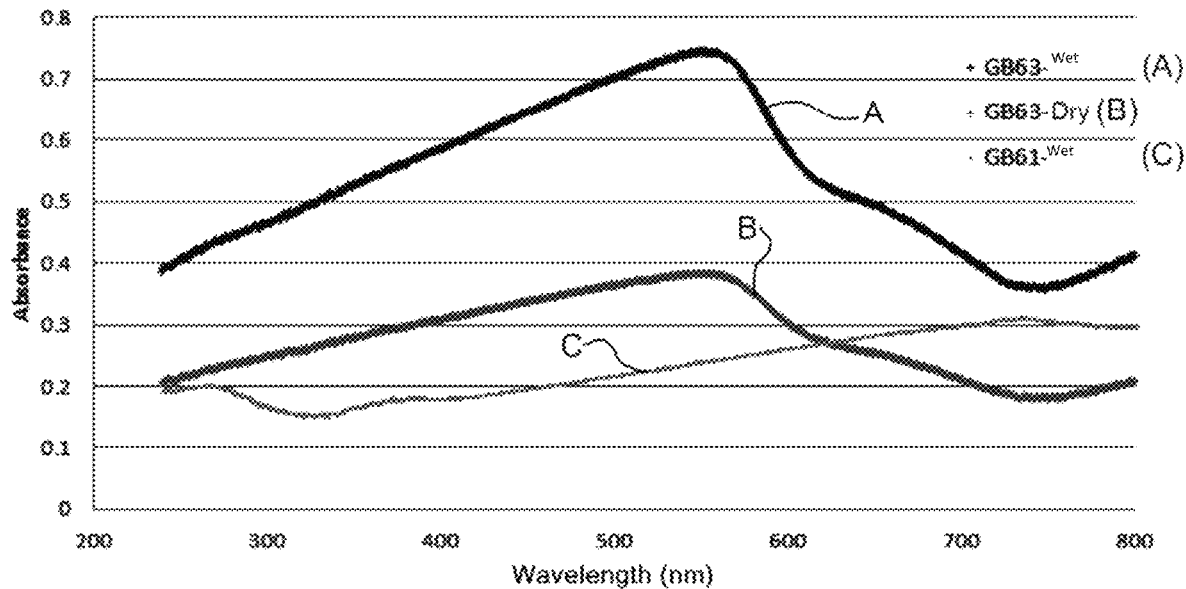

FIG. 8 is a graph which illustrates the UV and visible absorbance curves of the alkaline pigmented gel GB63 according to the invention, wet (curve A), of the pigmented gel GB63 according to the invention, dry (curve B), and of the wet white gel GB61 without any pigment, wet (curve C).

The wavelength (in nm) is plotted in abscissas, and the absorbance is plotted in ordinates.

Figure 9:
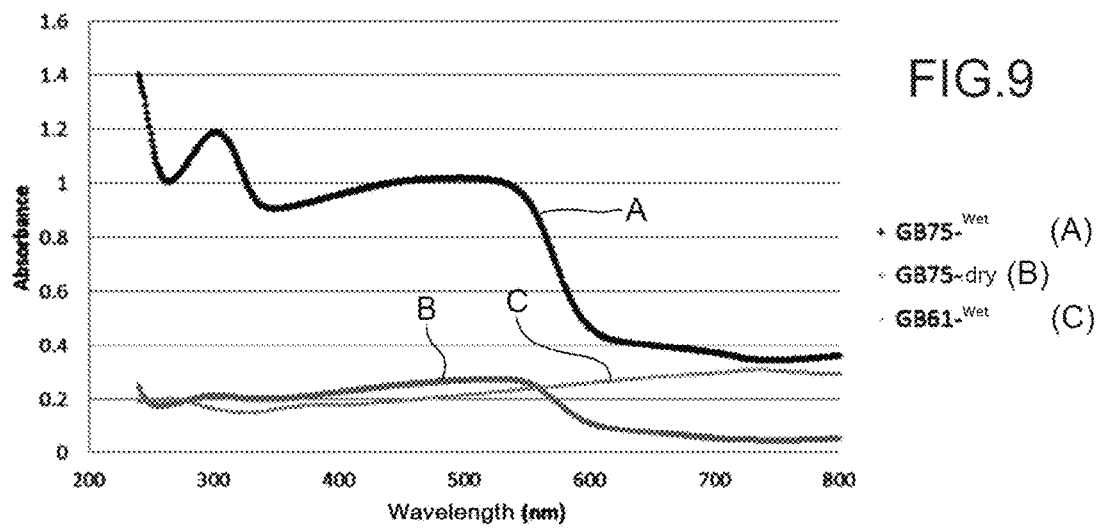

FIG. 9 is a graph which illustrates the UV and visible absorbance curves of the acid pigmented gel GB75 according to the invention, wet (curve A), of the pigmented gel GB75 according to the invention, dry (curve B), and of the wet white gel GB61 without any pigment, wet (curve C).

The wavelength (in nm) is plotted in abscissas, and the absorbance is plotted in ordinates.

Figure 10:
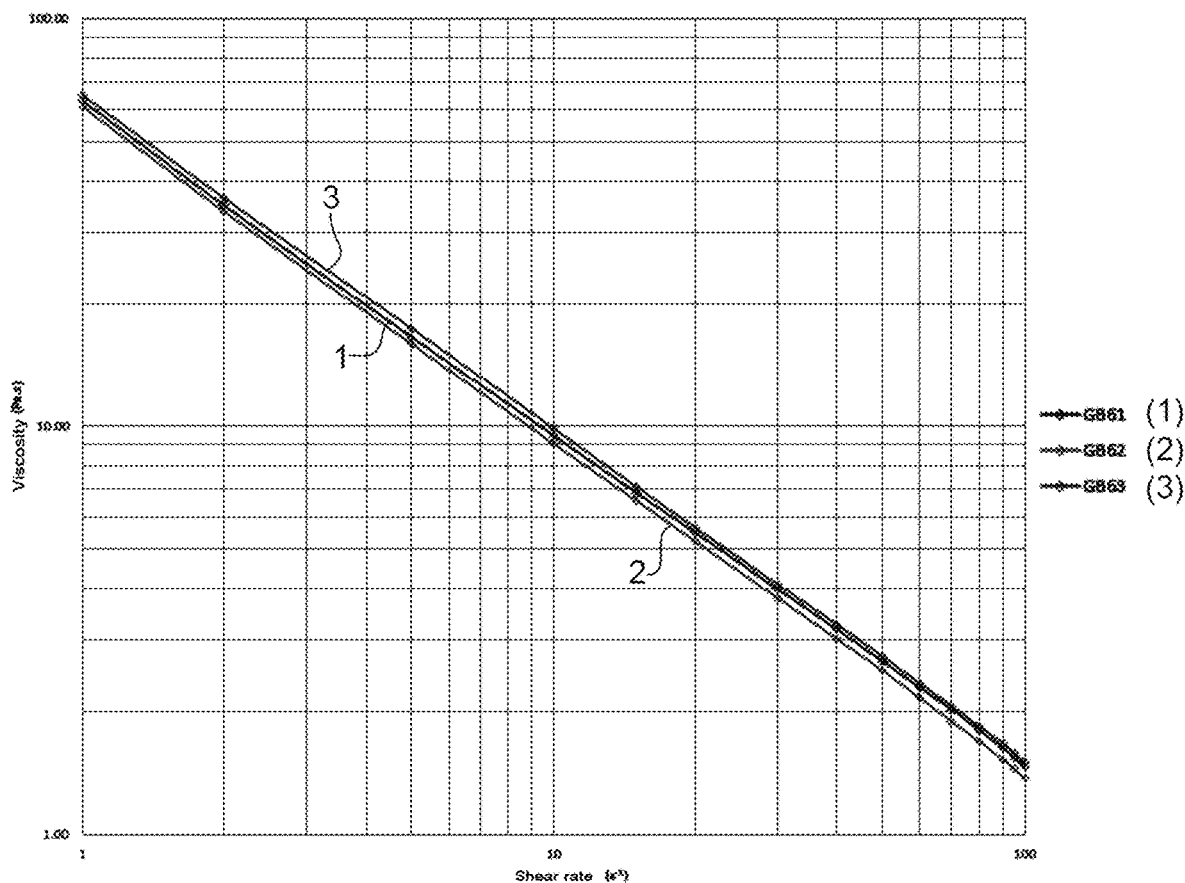

FIG. 10 is a graph which illustrates in a logarithmic scale, the viscosity (in Pa·s) of the GB61 (curve 1), GB62 (curve 2) and GB63 (curve 3) gels versus the shear rate (in $s^{-1}$).

Figure 11:
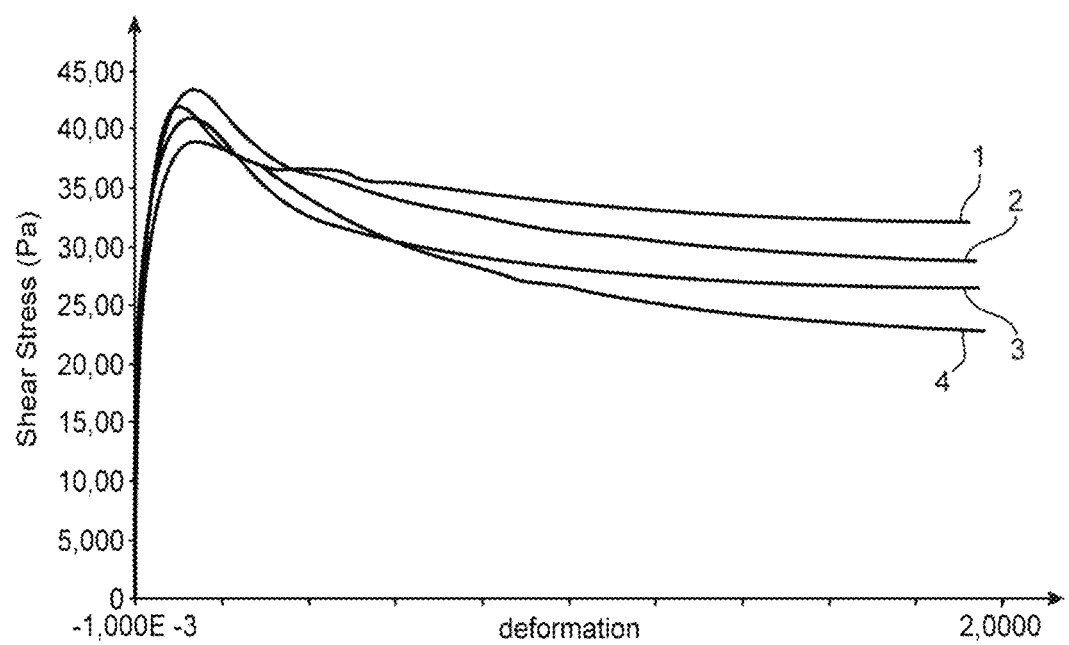

FIG. 11 is a graph which illustrates the threshold stress of the GB61 gel.

The curves 1, 2, 3, and 4 respectively represent the stress measured for pre-shearing at 100 $s^{-1}$ for 100 s, and then a rest period of 10 s (curve 1), a rest period of 100 s (curve 2), a rest period of 500 s (curve 3), and a rest period of 1,000 s (curve 4).

The deformation is plotted in abscissas and the stress (in Pa) is plotted in ordinates.

Figure 12:
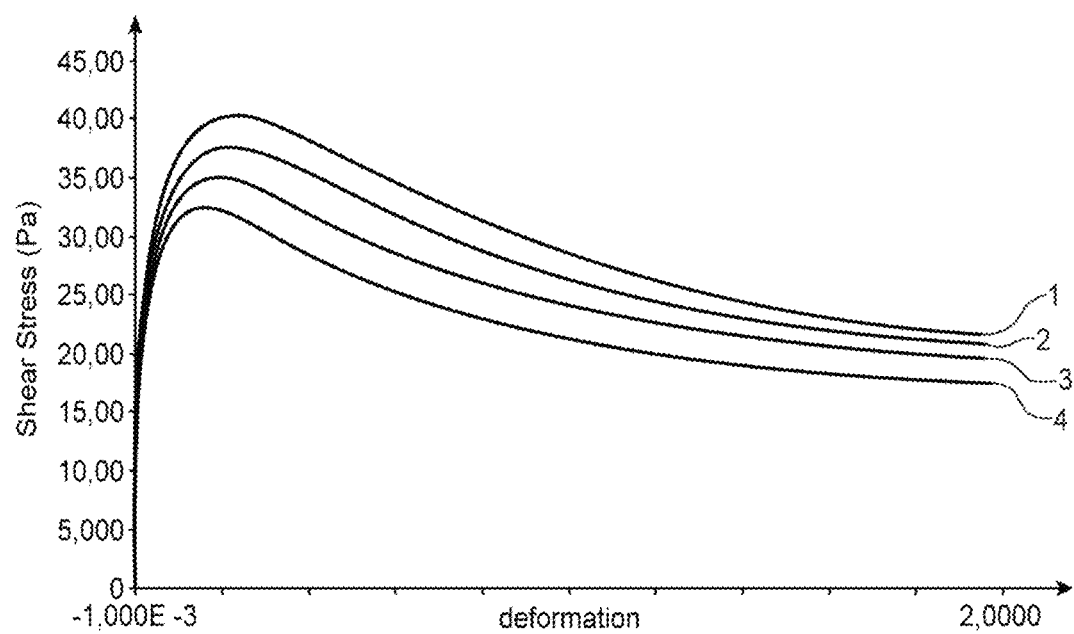

FIG. 12 is a graph which illustrates the threshold stress of the GB62 gel.

The curves 1, 2, 3, and 4 respectively illustrate the measured stress for pre-shearing at 100 $s^{-1}$ for 100 s, and then a rest period of 10 s (curve 1), a rest period of 100 s (curve 2), a rest period of 500 s (curve 3), and a rest period of 1,000 s (curve 4).

The deformation is plotted in abscissas and the stress (in Pa) is plotted in ordinates.

Figure 13:
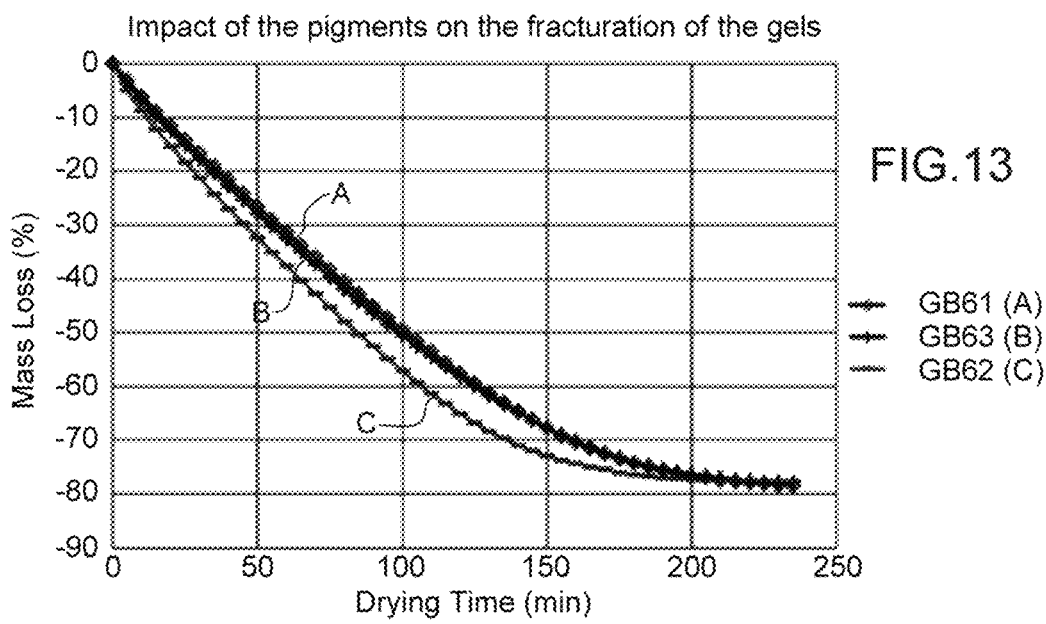

FIG. 13 is a graph which illustrates the drying kinetics of the GB61 (curve A), GB62 (curve B), and GB63 (curve C) gels.

The drying time (in mins) is plotted in abscissas and the mass loss (in %) is plotted in ordinates.

Figure 14:
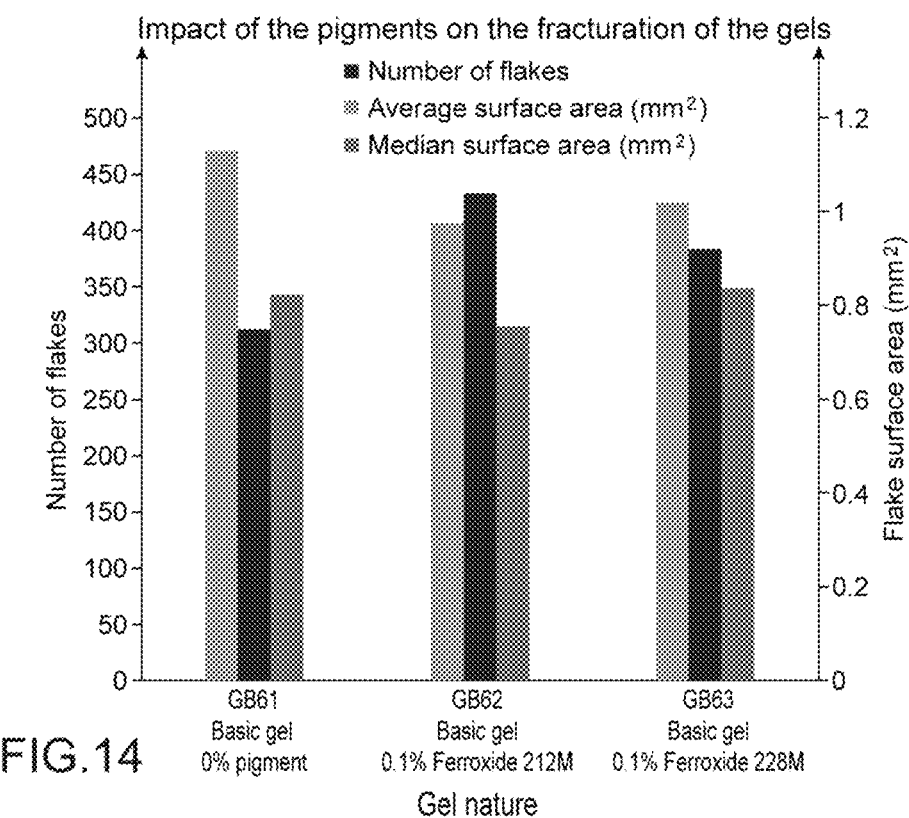

FIG. 14 is a graph which shows the fracturation of the GB61, GB62, and GB63 gels.

For each gel GB61, GB62, and GB63, the average area of the flakes (left bar), the number of flakes (middle bar), and the median area of the flakes (right bar) are given.

On the left scale, the number of flakes is plotted, and on the right scale the area of the flakes (in $mm^2$) is plotted.

Figure 15:
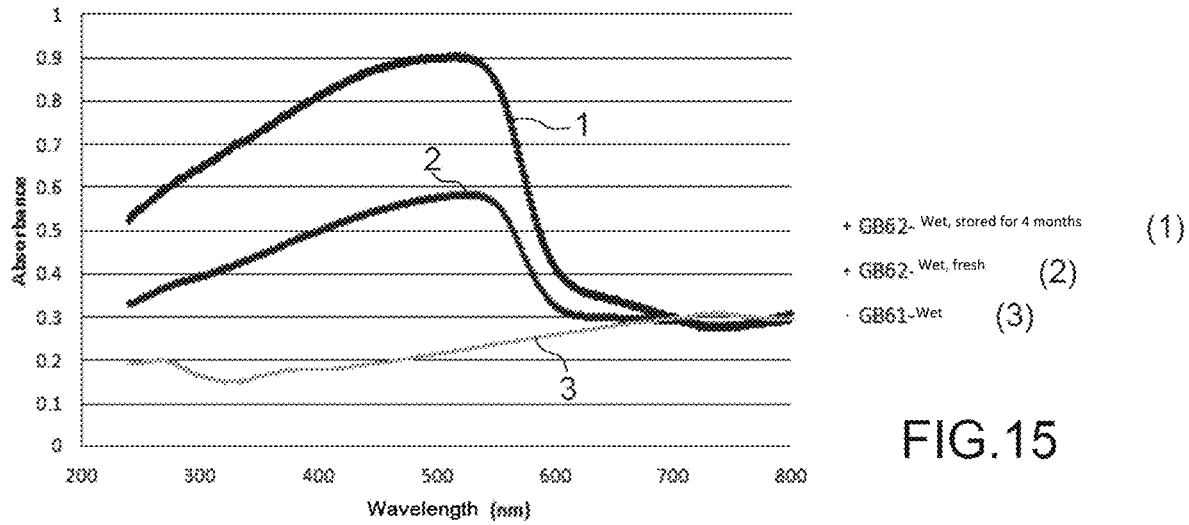

FIG. 15 is a graph which illustrates the UV and visible absorbance of the pigmented alkaline gel GB62 according to the invention, wet, fresh which has just been prepared (curve 2), of the pigmented alkaline gel GB62 according to the invention, wet, after storage for 4 months after its preparation (curve 1) and of the wet non-pigmented alkaline gel GB61 (curve 3).

The wavelength (in nm) is plotted in abscissas, and the absorbance is plotted in ordinates.

Figure 16A:
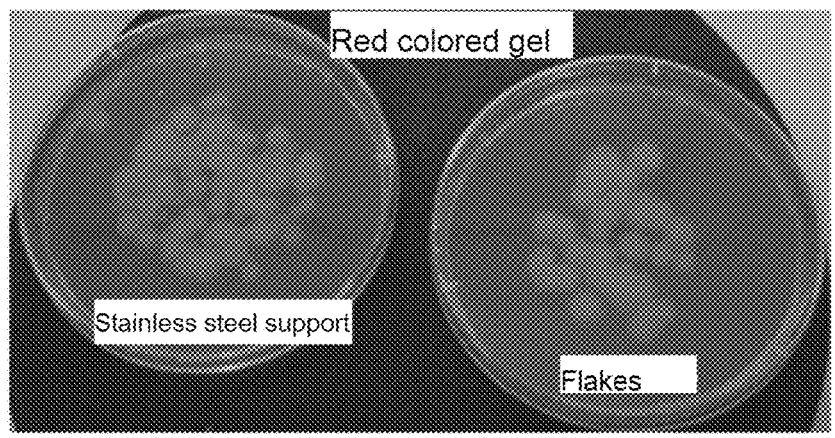
Figure 16B:
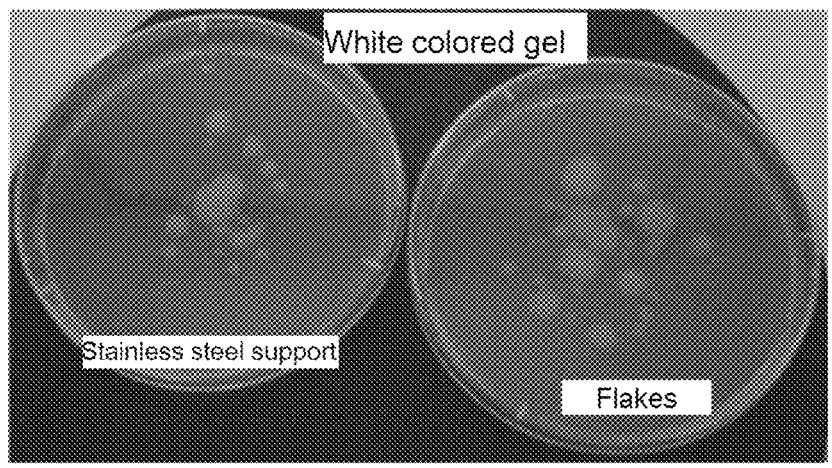

FIG. 16 shows photographs of Petri dishes in which were produced cultures from the decontamination of supports made of stainless steel contaminated by *Bacillus thuringiensis* with the pigmented gel GB62 according to the invention (16A) and by a non-pigmented white gel (16B).

In each of FIGS. 16A and 16B, the left Petri dish is a Petri dish containing a culture from the decontaminated support cleared of the flakes, while the right Petri dish is a Petri dish containing a culture from dry gel flakes recovered on the support.

DETAILED DISCUSSION OF PARTICULAR EMBODIMENTS

The gel according to the invention may easily be prepared at room temperature.

For example, the gel according to the invention may be prepared by preferably gradually adding the inorganic viscosifying agent(s), for example the alumina(s) and/or the silica(s), to a mixture of the active decontamination agent, of the optional surfactant(s), and of mineral pigment(s) such as iron oxides.

This mixture may be produced by mechanical stirring, for example by means of a mechanical stirrer equipped with a three-blade propeller. The speed of rotation is for example 200 revolutions/minute, and the duration of the stirring is for example from 3 to 5 minutes.

The addition of inorganic viscosifying agent(s) to the mixture containing the active biological decontamination agent, the optional surfactant(s), and the pigment(s) may be carried out by simply pouring the viscosifying agent(s) into the mixture. During the addition of the inorganic viscosifying agent(s), the mixture containing the active biological decontamination agent, the optional surfactant(s) and the pigment(s) is generally maintained with mechanical stirring.

This stirring may for example be produced by means of a mechanical stirrer equipped with a three-blade propeller.

The stirring speed is generally gradually increased as the viscosity of the solution increases, in order to finally attain a stirring rate comprised for example between 400 and 600 rpm, without there having been projections.

After the end of the addition of the mineral viscosifying agent(s), stirring is further maintained, for example for 2 to 5 minutes, so as to obtain a perfectly homogenous gel.

It is quite obvious that other procedures for preparing gels according to the invention may be applied with addition of the components of the gel in a different order from that mentioned above.

Generally, the gel according to the invention should have a viscosity of less than 200 mPa·s under shearing of 1,000 $s^{-1}$ so as to allow spraying onto the surface to be decontaminated, at a distance (for example at a distance from 1 to 5 m) or near (for example at a distance of less than 1 m, preferably from 50 to 80 cm). The viscosity resumption time should generally be less than one second and the viscosity under low shearing should be greater than 10 Pa·s so as to not run over a wall.

It should be noted that the surfactant of the gel according to the invention favorably influences notably the flow properties of the gel according to the invention. This surfactant notably gives the possibility of being able to apply the gel according to the invention by spraying and avoiding spreading or run-off risks upon treating vertical surfaces and ceilings.

The thereby prepared gel according to the invention is then applied (1) (FIG. 1A) on the solid surface (2) to be decontaminated of a substrate in a solid material (3), in other words on the surface (2) having been exposed to contamination for example to biological contamination (4). This contamination has already been described above. In particular, the biological contamination (4) may consist of one or several of the biological species already defined above.

As already indicated above, the active decontamination agent, for example the active biological decontamination agent, is selected according to the contaminating species, for example to the biological species to be removed (eliminated), destroyed, or inactivated.

Optionally except for light weight metal alloys of the aluminium type, in the case when basic or acid gels are applied, no limitation exists as to the material which constitutes the surface (2) to be decontaminated, indeed, the gel according to the invention gives the possibility of treating without any damage all kinds of material even brittle materials.

The gel according to the invention does not generate any alteration, erosion, chemical, mechanical or physical attack of the treated material. The gel according to the invention is therefore by no means detrimental to the integrity of the treated materials and even allows their reuse. Thus, sensitive equipment such as military equipment are preserved and may after their decontamination be reused, while monuments treated with the gel according to the invention are absolutely not degraded and their visual and structural integrity is preserved.

This material of the substrate (3) may therefore be selected from for example metals and alloys such as stainless steel, aluminium, and lead; polymers such as plastic materials or rubbers from among which mention may be made of PVC, PP, PE notably HDPE, PMMA, PVDF, PC; glasses; cements and cement materials; mortars and concretes; plasters; bricks; natural or artificial stone; ceramics.

In every case, regardless of the material, the decontamination efficiency with the gel according to the invention is total.

The treated surface may be painted or not painted.

In a particularly surprising way, it was found that the gel according to the invention, when it contained a super-absorbent polymer, was particularly efficient on porous materials such as cement matrices like slurries, mortars and concretes, bricks, plasters or further natural or artificial stone.

Indeed, the presence in the gel according to the invention of a super-absorbent polymer allows decontamination of a porous material over a much larger depth than with an equivalent gel without any super-absorbent polymer.

In other words, the presence of a super-absorbent polymer in the gel according to the invention facilitates the diffusion of the active decontamination agent, for example of the biocidal agent in the depth of the material when the question is to treat porous, notably mineral substrates.

The efficiency of the treatment with the gel according to the invention is generally total, including on materials contaminated over several millimetres of depth; in the latter case, a super-absorbent polymer is then preferably included in the gel.

Also there is no limitation as to the shape, the geometry and the size of the surface to be decontaminated, the gel according to the invention and the method applying it gives the possibility of treating surfaces of large size, with complex geometries, for example having cavities, recesses, angles, corners.

The gel according to the invention ensures efficient treatment not only of horizontal surfaces such as floors, but also of vertical surfaces such as walls, or of tilted or overhanging surfaces such as ceilings.

As compared with decontamination methods, for example existing biological decontamination methods which apply liquids such as solutions, the decontamination method according to the invention which applies a gel is particularly advantageous for treating materials with a large surface, which are not transportable and implanted outdoors. Indeed, the method according to the invention because of the application of the gel, allows decontamination in situ by avoiding the spreading of chemical solutions in the environment and dispersion of the contaminating species.

The gel according to the invention may be applied on the surface to be treated with any application methods known to the man skilled in the art.

Standard methods are spraying for example with a gun or application by means of a brush, a trowel.

For applying the gel according to the invention by spraying on the surface to be treated, the colloidal solution may for example be conveyed via a low pressure pump, for example a pump which applies a pressure of less than or equal to 7 bars, i.e. about $7 \cdot 10^5$ Pascals.

The bursting of the gel jet on the surface may for example be obtained by means of a nozzle with a flat jet or with a round jet.

The distance between the pump and the nozzle may be any distance, for example it may be from 1 to 50 m, notably from 1 to 25 m.

The sufficiently short viscosity recovery time of the gels according to the invention allow the sprayed gels to adhere to any surfaces, for example walls.

The amount of gel deposited on the surface to be treated is generally from 100 to 2,000 g/m², preferably from 500 to 1,500 g/m², still preferably from 600 to 1,000 g/m².

The deposited gel amount per unit surface and consequently the thickness of the deposited gel has an influence on the drying rate.

Thus, when a gel film, layer with a thickness of 0.5 mm to 2 mm is sprayed on the surface to be treated, the effective contact time between the gel and the materials is then equivalent to its drying time, a period during which the active ingredient contained in the gel will interact with the contamination.

In the case of porous substrates, for example cement matrices, the action time of the decontamination solution, for example of the biocidal solution—which in this case preferably contains a super-absorbent polymer having penetrated the core of the material—following the action of the super-absorbent polymer may be greater than the drying time of the gel, in which case it is generally necessary either to produce re-wetting with the contamination solution, for example with the biocidal solution, or repeat spraying of the gel.

Further, it was shown surprisingly that the deposited amount of gel when it is located in the ranges mentioned above and in particular when it is greater than 500 g/m² and notably in the range from 500 to 1,500 g/m², which corresponds to a minimum thickness of deposited gel for example greater than 500 µm for a deposited amount of gel of more than 500 g/m², after drying the gel gave the possibility of obtaining fracturation of the gel in the form of millimetric flakes, for example with a size from 1 to 10 mm, preferably from 2 to 5 mm, and vacuumable.

The deposited amount of gel and therefore the thickness of deposited gel preferably greater than 500 g/m² i.e. 500 µm, is the fundamental parameter which influences the size of the dry residues formed after drying the gel and which thus ensures the formation of dry residues with millimetric size and not powdery residues, such residues being easily removed by a mechanical method and preferably by suction.

However, it should also be noted that by means of the surfactant agent at a low concentration, generally from 0.1% to 2% of the total mass of the gel, the drying of the gel is improved and leads to a homogenous fracturation phenomenon with a size of mono-dispersed dry residues and increased capability of the dry residues to be detached from the support.

The gel is then maintained on the surface to be treated during the whole period required for its drying. During this drying step, which may be considered as the active phase of the method according to the invention, the solvent contained in the gel, i.e. generally the water contained in the gel evaporates until a dry and solid residue is obtained.

The drying duration depends on the composition of the gel in the concentration ranges of its constituents given above, but also, as already specified, on the deposited amount of gel per unit of area, i.e. the thickness of deposited gel.

The drying duration also depends on weather conditions, i.e. the temperature and the relative wetity of the atmosphere in which the solid surface is found.

The method according to the invention may be applied under extremely wide weather conditions, i.e. at a temperature T from 1° C. to 50° C. and at a relative wetity RH from 20% to 80%.

The drying duration of the gel according to the invention is therefore generally from 1 hour to 24 hours at a temperature T from 1° C. to 50° C. and at a relative wetity RH from 20% to 80%.

It should be noted that the formulation of the gel according to the invention essentially because of the presence of surfactants such as "Pluronics®" generally ensures a drying period which is substantially equivalent to the contact time (between the decontamination agent, such as a biocidal agent, and the contaminating species, for example the notably biotoxic biological species to be removed) which is necessary, required for inactivating and/or absorbing the contaminating species polluting the material, and/or for carrying out sufficiently the reactions for erosion of the surface of the material.

In other words, the formulation of the gel ensures a drying period time which is nothing else than the inactivation period time of the contaminating species, for example of the biological species, which is compatible with the contamination inhibition kinetics, for example of the biological contamination.

Or else the formulation of the gel ensures a drying period time which is nothing else than the period time required for the erosion reactions to remove a contaminated surface layer of the material.

In the case of radioactive contaminating species, the contamination is removed by dissolving irradiating deposits or by corrosion of the materials supporting the contamination. Therefore there is really a transfer of the nuclear contamination to the flakes of dry gels.

The specific surface area of the mineral filler generally used which is generally from 50 m²/g to 300 m²/g, preferably 100 m²/g and the absorption capacity of the gel according to the invention give the possibility of trapping the labile contamination (surface contamination) and attached to the material constituting the surface to be treated.

If required, the contaminating species, for example the contaminating biological species are inactivated in the gel phase. After drying the gel, the contamination, for example the inactivated biological contamination, is removed (eliminated) upon recovering the dry gel residue described below.

Figure 1:
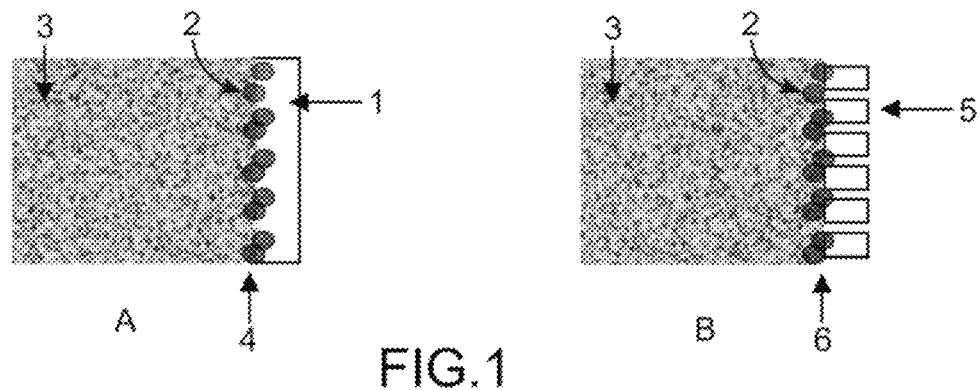
FIG. 1 (A, B) shows schematic sectional views illustrating the main steps of the method according to the invention for decontaminating a solid material.

At the end of the drying of the gel, the gel homogeneously fractures and gives millimetric solid dry residues, for example with the size from 1 to 10 mm, preferably from 2 to 5 mm, which are not powdery, and generally are as solid flakes (5) (FIG. 1B).

The dry residues may contain the inactivated contaminating species (6).

The dry residues, such as flakes (5), obtained at the end of the drying have low adherence to the surface (2) of the decontaminated material. Consequently, the dry residues obtained after drying the gel may easily be recovered by simple brushing and/or suction.

However, the dry residues may also be discharged by a gas jet, for example by a compressed air jet.

Thus, no rinsing with a liquid is generally necessary, and the method according to the invention does not generate any secondary effluent.

However, it is possible, although this is not preferred, and if this is desired, to remove the drying residues by means of a liquid jet.

The method according to the invention thus therefore achieves first of all significant savings in chemical reagents as compared with a decontamination method by washing with a solution. Subsequently, because a waste as a dry residue which is directly vacuumable is obtained, a rinsing operation with water or with a liquid generally required for removing trace amounts of chemical agents from the part is generally avoided. The result of this is quite obviously a reduction in the amount of produced effluents but also a notable simplification in terms of waste treatment system and outlet.

Because of the in majority mineral composition of the gel according to the invention and of the small amount of produced wastes, the dry waste may be stored or directed to a discharge system ("outlet") without any prior treatment.

The dry gel flakes obtained at the end of the method according to the invention have been approved at ANDRA as a heterogeneous waste which may be immobilized in an HTC mortar grout.

At the end of the method according to the invention, a solid waste is recovered as flakes which may be conditioned as such, directly conditioned, the result of this, as already indicated above is a significant reduction in the amount of produced effluents as well as notable simplification in terms of waste treatment system and outlet.

Further, in the nuclear field, the fact of not having to reprocess the flakes after conditioning the waste is a considerable advantage; this authorizes the use of active performing agents which were banned up to now, in decontamination liquids because of the constraints on operating stations for processing liquid effluents ("LETS").

The gel may therefore contain powerful oxidizers such as cerium IV which may very easily be regenerated from electrolysis of cerium III.

As an example, in the current case where 1,000 grams of gel per m² of treated surface are applied, the produced dry waste mass is less than 200 grams per m².

Figure 2:
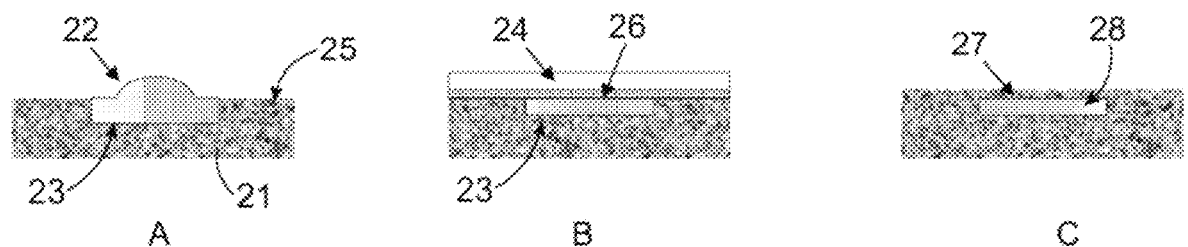
FIG. 2 (A, B, C) shows schematic sectional views showing the mode of action of a gel without any super-absorbent polymer on a cement material contaminated in depth by a contamination in liquid form.

In FIG. 2, the decontamination with a gel not containing any super-absorbent polymer of a porous substrate (21) for example contaminated with spores in an aqueous solution (22) is illustrated. The contamination front (23) extends into the depth of the substrate (FIG. 2A). When a decontamination gel, for example a biocidal gel (24) is applied on the surface (25) of the substrate, the diffusion front (26) of the decontamination agent, for example the biocidal agent, does not extend much into the depth of the substrate and remains below the contamination front (23) (FIG. 2B). Consequently, when the gel is removed (FIG. 2C), the cleaned-up area (27) does not extend much in depth and a residual contamination (28) remains in the porous substrate (21).

Figure 3:
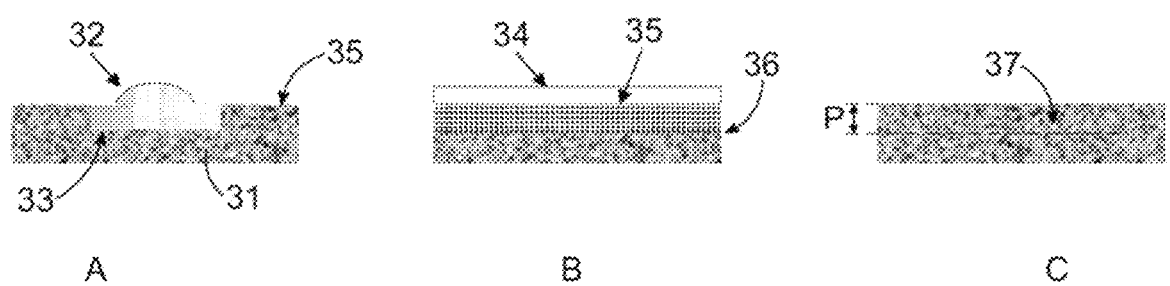
FIG. 3 (A, B, C) shows schematic sectional views showing the mode of action of a gel containing a super-absorbent polymer on a cement material contaminated in depth by a contamination in liquid form.
Figure 4:
FIG. 4 is a photograph which shows the spraying of a conventional non-pigmented white decontamination gel on a support to be decontaminated consisting of white ceramic tiles. This photograph shows that it is difficult to distinguish the areas covered by the gel, whether they are dry or wet, from the areas which are not covered by the gel.
Figure 5:
FIG. 5 is a photograph which shows a wall of ceramic tiles of the Paris Metro covered with a white non-pigmented gel.
Figure 6:
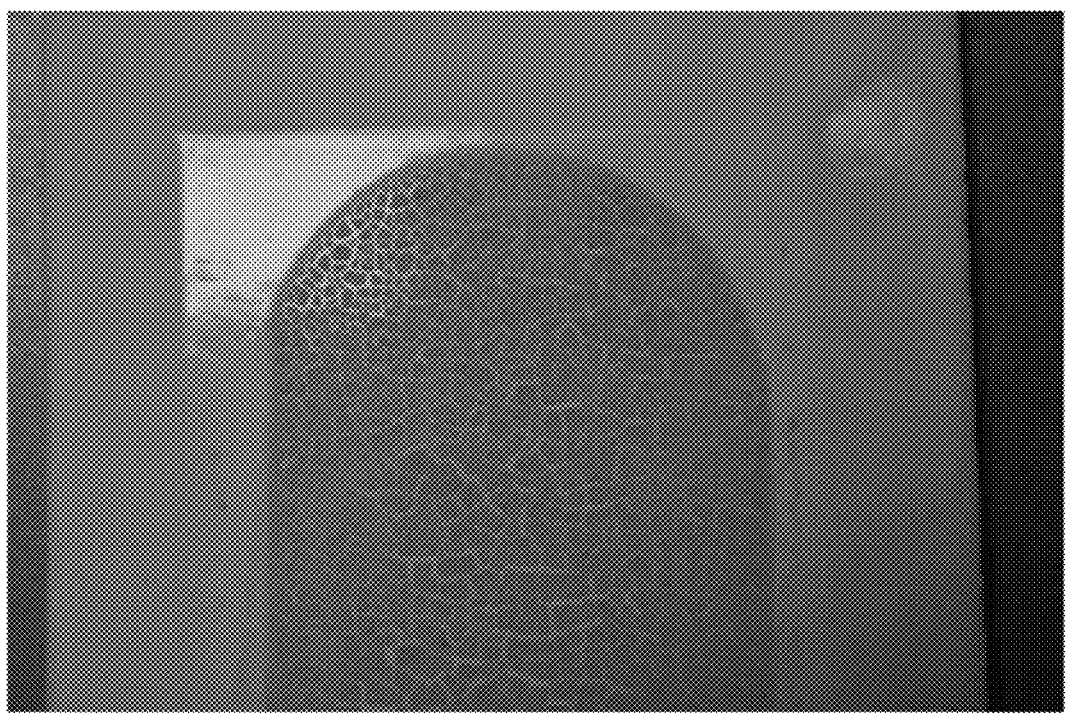
FIG. 6 is a photograph which shows a ceramic tile covered with pigmented gel according to the invention, dry and fractured.

In FIG. 3, the decontamination with the gel according to the invention containing a super-absorbent polymer, of a contaminated porous substrate (31), for example with spores in an aqueous solution (32) is illustrated. The contamination front (33) extends into the depth of the substrate (FIG. 3A). When a decontamination gel, for example a biocidal gel containing the super-absorbent (34) is applied on the surface (35) of the substrate, the diffusion front (36) of the decontamination agent, for example of the biocidal agent extends into the depth of the substrate and goes beyond the contamination front (33) (FIG. 3B). Consequently, the cleaned-up area (37) extends in depth (P) and there no longer remains any residual contamination in the porous substrate.

The invention will now be described with reference to the following examples given as an illustration and not as a limitation.

EXAMPLES

Example 1

In this example, the discoloration of basic gels is studied during their drying.

The gels analyzed in this example are basic mineral gels consisting of 14% of Aeroxide® Alu C alumina marketed by EVONIK INDUSTRIES and having a specific surface area of 100 m²/g (BET), of 0.2% of surfactants (Pluronic® PE6200 from BASF, and Empilan® KR8 from HUNTSMAN), and the balance 1M soda.

According to these gels (Table 1), the formulation may also contain a pigment, i.e. 0.1% by mass of micronized red iron oxides Ferroxide® from Rockwood Pigments Ltd of formula $Fe_2O_3$ with an average particle size of 0.1 µm or 0.5 µm.

The surfactants, the optional iron oxides, and the soda are first of all mixed by means of a mechanical stirrer provided with a three-blade stirrer at a rate of 200 rpm for 3 to 5 minutes.

The alumina is then gradually added into the reaction mixture by gradually increasing the stirring as the viscosity increases so as to reach about 400 to 500 rpm without there being any projections. The gel is then maintained with stirring for 5 minutes.

The thereby manufactured gels are then analyzed in the wet condition and in the dry condition by means of a UV-3600 Shimadzu® spectrometer in order to measure their UV-Visible light absorbance by reflection. The measurements are conducted in the wavelength range from 240 to 800 nm. The base line is produced on a barium sulfate tablet.

Three gels designated as GB61, GB62, and GB63 were prepared, the coloration of these gels is indicated in Table 1 below.

TABLE 1

Coloration of the tested gels.

| GEL | PIGMENT | COLOR |
| --- | --- | --- |
| GB61 | 0% | White gel |
| GB62 | 0.1% Ferroxide ® Rockwood 212M (average particle size: 0.1 µm) | Red gel |
| GB63 | 0.1% Ferroxide ® Rockwood 228M (average particle size: 0.5 µm) | Violet/mauve gel |

The absorbance of the GB61 white gel without any pigment is measured only in the wet condition.

On the other hand, for the two colored gels GB62 and GB63 according to the invention, the absorbance of the wet gels but also that of the flakes obtained at the end of their drying is measured.

In order to achieve analyses on wet gels, they are deposited on the support of the spectrometer placed vertically for the period of analysis. The gels adhere to the walls of the analysis chamber.

In order to achieve the analyses on dry flakes, the latter are milled with a mortar in order to obtain a powder. The powder is then deposited on a barium sulfate tablet, and then compacted before being placed vertically in the analysis chamber.

Figure 7:
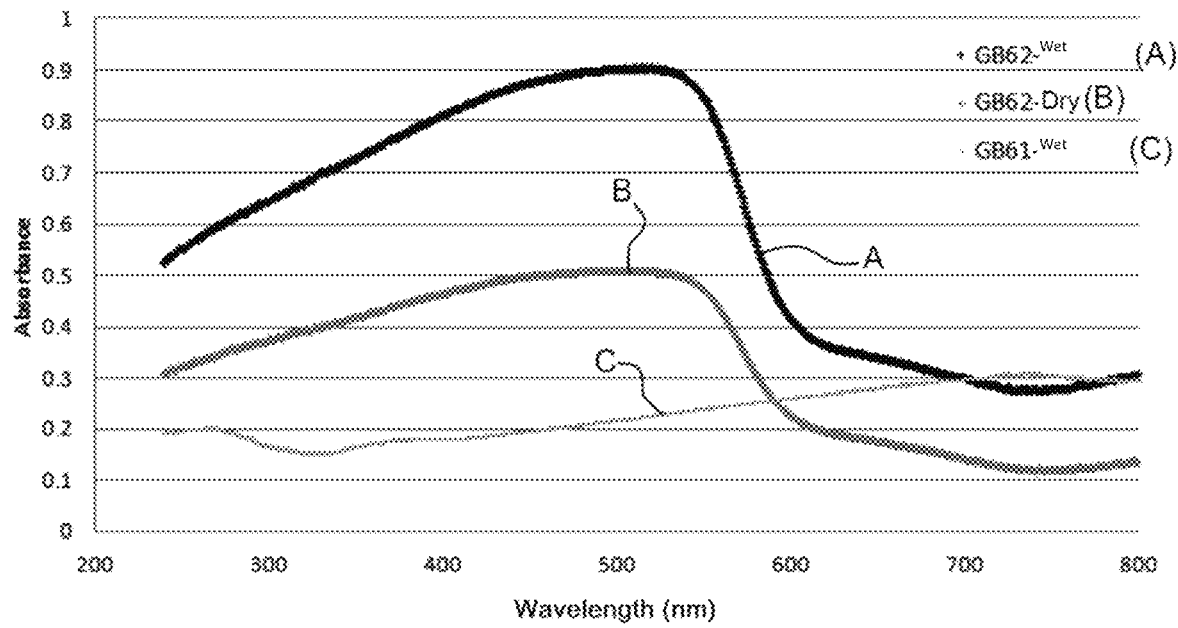
FIG. 7 is a graph which illustrates the UV and visible absorbance curves of the alkaline pigmented gel GB62 according to the invention, wet (curve A), of the pigmented gel GB62 according to the invention, dry (curve B), and of the wet white gel without any pigment GB61, wet (curve C).

The results of the analyses are shown in FIGS. 7 and 8.

First of all, it obviously appears that the pigmented, colored gels GB62 and GB63, according to the invention, have higher absorbances than the white gel GB61 without any pigment.

In spite of a low concentration of pigments (0.1%), it is easy to appreciate the strong coloration of these gels according to the invention, related to the strong coloring power of red iron oxide pigments.

Depending on the surface to be decontaminated which has to be covered with the gel, this strong coloration of the gels according to the invention is a particularly advantageous property for operators in NRBC overalls. Indeed, it for example gives the possibility of avoiding the shade-over-shade effect in the areas with reduced visibility and it thus facilitates visual detection of the areas either covered or not by the gel.

Moreover, comparison of the absorbance of the wet gels and of the dry flakes obtained after drying these gels, gives the possibility of demonstrating that the desired goal in terms of decontamination has actually been reached.

Indeed, the absorbance of the dry gel flakes is not as strong as that of wet gels, the absorbance curves however having completely similar aspects.

This lower absorbance of the flakes expresses a discoloration of the gel during drying, and confirms the results of the visual observations.

This discoloration, related to the addition of pigments in the gels according to the invention, is one of the main advantageous effects obtained with the gels according to the invention, since it gives the possibility of easily and rapidly identifying the wet areas and the dry areas on the surfaces covered with the decontamination gels according to the invention.

It should be noted that the aspect of the absorbance curves depends on the pigment present in the gel.

Indeed, the absorbance curves obtained with the gel containing the wet or dry red Ferroxide 212M pigment as flakes have the same aspect, and this aspect is different from that of the absorbance curves obtained with the gel containing the wet or dry violet Ferroxide 228M pigment as flakes.

Example 2

In this example, the discoloration of an acid gel according to the invention is studied during its drying.

A colored acid gel is formulated, containing red iron oxide pigments in order to show that discoloration during drying also occurs when the gel is an acid gel.

This gel, called gel GB75, consists of 14% of silica Tixosil® 331 marketed by RHODIA which has a specific surface area of 200 m$^2$/g (BET), 0.2% of surfactants (Pluronic® PE6200 from BASF, and Empilan® KR8 from HUNTSMAN), 0.1% of micronized red iron oxides Ferroxide® 212M from ROCKWOOD PIGMENTS LTD of formula $Fe_2O_3$, and the balance 1N nitric acid.

The gel is manufactured according to the same method as in Example 1.

The wet and dry GB75 gels are analyzed with a spectrometer UV-3600 Shimadzu® according to the same method as in Example 1.

The results of these analyses are shown in FIG. 9.

It appears, like in Example 1, that the acid gel GB75 is more colored than the white basic gel GB61 without any pigment.

Further, the GB75 acid gel flakes have lower absorbance than that of the same wet gel, which again shows the discoloration of the gel subsequent to drying.

This example shows that the gels according to the invention may both be basic gels and acid gels which in both cases have the same advantageous properties.

Example 3

In this example, the rheology of the pigmented gels according to the invention is studied.

More specifically, in this example the flow properties of both colored basic gels GB62 (red) and GB63 (violet) according to the invention described in Example 1 are compared, as well as the flow properties of the GB61 white basic gel without any pigments described in Example 1, in order to observe the impact of the addition of pigments at 0.1% by mass on the viscosity of the gel.

Indeed, it is indispensable that the rheological properties of the gel, which is a so called "sprayable" gel should be retained so that said gel may be sprayed and always adheres to the support.

Thus, it should be checked that the addition of micronized particles—in this case pigments—does not modify at all the viscosity of the colloidal gel which itself consists of alumina aggregates of a micrometric size.

For this, two viscosimetric and rheological measurements are conducted.

The first measurement which may be described as a viscosimetric measurement, consists of measuring the viscosity versus the shearing rate by means of a viscosimeter Rheomat® RM100 from LAMY RHEOLOGY.

The viscosimeter is equipped with a measurement system of the MS-R3 anchor type. After 10 second pre-shearing at a shearing rate of 1 s$^{-1}$, 15 plateaus of a shear rate ranging from 1 s$^{-1}$ to 100 s$^{-1}$ are carried out with a measurement of the viscosity every 20 seconds.

The second measurement, which may be described as a rheological measurement, consists of measuring the threshold stress of the GB61 and GB62 gels by means of a rheometer TA Instruments AR-1000 in a "Vane" geometry.

A low shearing rate, i.e. 6.7×10$^{-3}$ s$^{-1}$, is applied to the gels in a constant way in order to deform them from rest, and thus determine their flow threshold.

The results of the viscosimetric measurements on the GB61, GB62, and GB63 gels are illustrated in a logarithmic scale in FIG. 10.

FIGS. 11 and 12 as for them illustrate the results of rheological measurements.

In FIG. 10 it appears that the three curves are very close and parallel.

In this range of shearing rates, it is therefore impossible to perceive a difference from a rheological point of view, between the white gel without any pigment and the gels according to the invention containing 0.1% by mass of red iron oxide pigments.

Thus, the addition of a small amount of micronized pigments does not fundamentally change the rheology of the colloidal mineral gels.

FIG. 11 and FIG. 12 illustrate the shear stress, versus deformation for the gels GB61 (FIG. 11) and GB62 (FIG. 12) respectively.

In both cases, two regimes may be observed.

First of all, the stress increases linearly, the material is under a solid regime (elastic deformation).

A jump is then observed, the shear attains the flow threshold and the material switches to the liquid regime (stationary flow).

The threshold shear corresponds to the shear at the flow threshold, i.e. a maximum of 43 Pa for the GB61 gel, and a maximum of 40 Pa for the GB62 gel.

It should be noted that the measurements were conducted four times for each gel, i.e. for pre-shearing at 100 s$^{-1}$ for 100 s, followed by a rest period of 10 s (curve 1), 200 s (curve 2), 500 s (curve 3), and 1,000 s (curve 4). The reproducibility of the measurements is good.

Thus, it appears that the addition of pigment to the formulation has little influence on the threshold stress, and that the gel always meets the requirements sheet of "vacuumable gels," i.e. a threshold stress of more than 15-20 Pa so that the gel does not flow under the effect of gravity on a vertical wall for applied gel thicknesses of 0.5-2 mm.

Example 4

In this example, the drying kinetics of the pigmented gels according to the invention are studied.

Indeed, another fundamental characteristic of the decontamination gels is their drying time which is very closely related to the weather conditions of the drying environment, i.e. temperature, relative wetity, ventilation/aeration.

In this example, three basic gels GB61 (white, without any pigment), GB62 (red, pigmented according to the invention) and GB63 (violet, pigmented according to the invention), are dried one after the other in a weathering chamber Binder® adjusted to 25° C. and to 50% of relative wetity.

The gels are spread out on machined stainless steel boats, nacelles so as to obtain a controlled thickness of 0.5 mm of gel in the boat, nacelle.

In the weathering chamber, precision scales Sartorius are installed, as well as a Moticam® camera surrounded by a circular LED lamp (VWR®) which is placed above the scales. The scales and the Moticam camera are connected to a computer placed outside the weathering chamber thereby allowing simultaneous acquisition, during drying in a controlled atmosphere, of the mass and of the images of the boat, nacelle filled with gel.

It should be noted that the nacelle, boat, containing the gel is placed in the precision scales, and that all the doors of the scales are closed, except for the door opposite to the fan which is opened by 3 cm in order to maintain the controlled atmosphere in the chamber of the scales while limiting the air flow related to the operation of the weathering chamber.

The results, shown in FIG. 13, show a mass loss completely identical between the white GB61 gel without any pigment and the Ferroxide® 228M gel GB63 according to the invention.

Indeed, within 200 minutes, i.e. 3 h 20 min, the gel is completely dry and has lost at least a little less than 80%, i.e. 78% of its initial mass.

As regards the gel GB62 with Ferroxide® 212M according to the invention, the gel dries slightly more rapidly but the 78% mass loss plateau is attained within less than 200 minutes. This difference between the times required for attaining this plateau of mass loss of 78%, may be related to a slight variation in the opening of the door of the scale for example.

This example therefore shows that the addition of a small concentration of pigment to gels does not fundamentally change the drying kinetics of these gels both as regards the total drying time and the general aspect of the curves illustrating the drying kinetics of the gels.

Example 5

In this example, the fracturation of the pigmented gels according to the invention is studied.

Indeed, in addition to their rheology (so that they are sprayable and adherent) and their drying time, a third important feature of the decontamination gels, so called "vacuumable" gels, is their fracturation in the dry condition, in the form of non-powdery millimetric solid flakes.

Therefore in this example the question is of making sure that the addition of pigments in a gel does not modify in any way its fracturation.

This experiment is conducted in parallel with measurements conducted in Example 4 in a weathering chamber under a controlled atmosphere.

Indeed, during drying, according to the procedure and with the device detailed in Example 4, the images (FIG. 14) and the mass of the gel (FIG. 13) are simultaneously recorded during the drying of the gel in the nacelle. The Moticam camera regularly shoots images over time.

The photograph of the totally dry gel is then analyzed by means of an image processing piece of software which detects flakes and counts them while calculating their area.

The results are illustrated in FIG. 14.

Of course, the number of flakes is slightly greater for both gels GB62 and GB63 according to the invention which contains 0.1% of pigments than for the GB61 gel which does not contain any.

Nevertheless, the difference in terms of the number of flakes and of average area is not significant. The flakes have a millimetric size with an average size around 1 mm$^2$ as this is desired in the requirements specification of "vacuumable gels".

According to this example, the red iron oxide pigments therefore do not fundamentally alter, at such concentrations, the fracturation of the gel.

Example 6

In this example, it is shown that the coloration of the gels according to the invention is preserved over time.

More exactly, in this example, the question is to show that the coloration is constant between a gel stored for several weeks and a fresh gel which has just been prepared.

For this, two GB62 gels (red) are made according to the method described in Example 1, and they are then analyzed in the wet condition with the UV-3600 spectrometer according to the same method as in Example 1.

The first of these GB62 gels (red) is stored, kept for 4 months following its making, before conducting the analysis. This gel is called an old stored gel.

The second of these gels GB62 is made the day before the measurement. This gel is called a new, fresh gel.

The results of the analyses are shown in FIG. 15.

Both curves, respectively for the preserved gel and the fresh gel have a similar aspect since these gels contain the same Ferroxide® 212M pigment at the same concentration.

However, the fresh gel has much less significant absorbance than the old gel. This may be due to the strong coloring power of micronized red iron oxide pigments. Indeed, a very small difference in the mass of the added pigment (and this up to 0.1% by mass) may strongly modify the coloration of the pigmented gel.

Example 7

In this example, the biocidal properties of the gel according to the invention are studied.

Indeed, it should be checked that the biocidal properties of the gel are not altered by adding pigments in its formulation.

To do this, the biocidal efficiency of the GB62 pigmented gel according to the invention and of the GB61 white gel without any pigment are tested on a contaminating biological species, i.e. spores of *Bacillus thuringiensis*, non-pathogenic similar to the spores of *Bacillus anthracis*.

Under a hood with lamina flow and in a sterile way, two autoclaved stainless steel supports are contaminated with $10^7$ spores of *Bacillus thuringiensis* by carrying out a deposition of 100 µl of a liquid contaminating solution containing $10^8$ spores of *Bacillus thuringiensis* (B.T.) per ml.

Once the supports are dry, the gels to be tested are spread out on the supports with an average thickness of 0.6 mm and are left to dry under the hood for 3 h-3 h30 mins. Next, the dry gel flakes are brushed and recovered in 30 ml of a nutrient medium LB. Also, the supports cleared of the flakes are placed in tubes with 30 ml of nutrient medium LB. After 1 h of incubation of the tubes at 30° C. with stirring, 30 µl of LB are sampled in each of the tubes, and then spread at the centre of Petri dishes containing gelled LB. The dishes are then placed in the incubator at 30° C. for 24 h.

The obtained results are shown in FIG. 16 (A, B). It appears that the number of colonies present after 24 h of incubation on the surface of the gelled LB of the different dishes is of the same order of magnitude. Indeed, the development of a colony corresponds to the growth of a spore not inactivated by the biocidal gel.

By knowing that 30 µl on the 30 ml of the recovered LB medium were spread on the dishes, i.e. $1/1,000^{th}$, it may be estimated that on the 4 dishes shown, there remains after decontamination of the supports by the gel, about $10^4$ spores of active B.T. over the $10^7$ spores initially deposited on the supports, i.e. a lowering of 3 on a logarithm scale due to the effect of the gels, which are either pigmented or not (these biological counts have an accuracy to within a power of ten).

This example shows that the biocidal efficiency of the basic gel is therefore not significantly altered by the addition of red iron oxide pigments.

CONCLUSION FROM THE EXAMPLES

The examples provided above show that the addition of micronized iron oxide pigments to a decontamination gel provides an actual improvement for the application of the "vacuumable gel" technology within the scope of a post-event use, for example subsequent to an industrial accident, or a terrorist attack.

Indeed, the addition in the gels according to the invention of a small amount of pigments gives the possibility of improving viewing, by intervention teams in NRBC overalls, of areas of the surface of a contaminated material covered with the gel as compared with the other areas of the surface of this material.

Moreover, possible discoloration of the pigmented gel following the drying of the latter is another of the advantages of the pigmented gels according to the invention. Indeed, this discoloration gives the possibility of clearly and specifically evaluating the state of progression of the drying of the gel which goes together with the progress of the decontamination method. It is thus possible to ensure total and complete drying of the decontamination gel before its suction/conditioning.

These advantageous properties of the gels according to the invention, due to the presence in the gels according to the invention of mineral pigments and notably of micronized iron oxide pigments, are obtained without altering the physico-chemical properties of these gels which make them applicable within the scope of a so called "vacuumable gel" method. Indeed, the properties of fracturation and of drying the gels according to the invention as well as their viscosity and their threshold stress are not deteriorated by adding pigments.

REFERENCES

[1] CUER F., FAURE S., "Gel de décontamination biologique et method de décontamination de surfaces utilisant ce gel", FR-A1-2962046 and WO-A1-2012/001046.
[2] HOFFMAN D., Mc GUIRE R., "Oxidizer gels for detoxification of chemical and biological agents", U.S. Pat. No. 6,455,751.
[3] HARPER B., LARSEN L., "*A comparison of decontamination technologies for biological agents on selected commercial surface materials*", Biological weapons improved response program, April 2001.
[4] FAURE S., FOURNEL B., FUENTES P., LALLOT Y., "Method de traitement d'une surface par un gel de traitement, et gel de traitement", FR-A1-2 827 530.
[5] FAURE S., FUENTES P., LALLOT Y., "Gel aspirable pour la décontamination de surfaces et utilisation", FR-A1-2 891 470.

The invention claimed is:

1. A decontamination gel consisting of a colloidal solution comprising:
    0.1% to 30% by mass, based on the mass of the gel, of at least one inorganic viscosifying agent;
    0.1 to 10 mol/L of gel, of at least one active decontamination agent;
    0.01% to 0.1% by mass, based on the mass of the gel, of an iron oxide pigment;
    optionally, 0.1% to 2% by mass based on the mass of the gel, of at least one surfactant;
    optionally, 0.05% to 5% by mass, based on the mass of the gel, of at least one super-absorbent polymer;
    and the balance of solvent.

2. The decontamination gel according to claim 1, wherein the iron oxide pigment is selected so that it gives the gel a color different from the color of a surface to be decontaminated on which the gel is applied.

3. The decontamination gel according to claim 1, wherein the iron oxide pigment is a micronized pigment and the average size of the particles of the iron oxide pigment is from 0.05 to 5 µm.

4. The decontamination gel according to claim 1, wherein the inorganic viscosifying agent is selected from a group consisting of oxides of metals, oxides of metalloids, hydroxides of metals, hydroxides of metalloids, oxyhydroxides of metals, oxyhydroxides of metalloids, aluminosilicates, clays, and mixtures thereof.

5. The decontamination gel according to claim 4, wherein the inorganic viscosifying agent is selected from a group consisting of pyrogenated silicas, precipitated silicas, hydrophilic silicas, hydrophobic silicas, acid silicas, basic silicas, and mixtures thereof.

6. The decontamination gel according to claim 5, wherein the inorganic viscosifying agent consists of a mixture of precipitated silica and of a pyrogenated silica.

7. The decontamination gel according to claim 4, wherein the inorganic viscosifying agent consists of one or several aluminas representing from 5% to 30% by mass, based on the mass of the gel.

8. The decontamination gel according to claim 1, wherein the active decontamination agent is selected from a group consisting of bases, acids, oxidizers, quaternary ammonium salts, reducing agents, and mixtures thereof.

9. The decontamination gel according to claim 1, wherein the super-absorbent polymer is selected from a group consisting of sodium poly(meth) acrylates, starches grafted with a (meth)acrylic polymer, hydrolysed starches grafted with a (meth)acrylic polymer; polymers based on starch, on a gum, and on a cellulose derivative; and mixtures thereof.

10. The decontamination gel according to claim 1, wherein the surfactant is selected from non-ionic surfactants and mixtures thereof.

11. The decontamination gel according to claim 1, wherein the solvent is selected from a group consisting of water, organic solvents and mixtures thereof.

12. A method for decontaminating at least one surface of a substrate made of a solid material, said surface being contaminated with at least one contaminating species found on said surface and optionally under said surface in the depth of the substrate, wherein at least one cycle is carried out, comprising the following successive steps:
  a) applying the gel according to claim 1 on said surface;
  b) maintaining the gel on the surface for at least a sufficient duration so that the gel destroys and/or inactivates and/or absorbs the contaminating species, and so that the gel dries and forms a dry and solid residue containing said contaminating species;
  c) removing the dry and solid residue containing said contaminating species.

13. The method according to claim 12, wherein the iron oxide pigment contained in the gel is selected so that it gives the gel a color different from the color of the surface to be decontaminated on which the gel is applied.

14. The method according to claim 12, wherein the substrate is a porous substrate, optionally, a porous mineral substrate.

15. The method according to claim 12, wherein the solid material is selected from a group consisting of metals and metal alloys; polymers; glasses; cements and cement materials; mortars and concretes; plasters; bricks; natural or artificial stone; and ceramics.

16. The method according to claim 12, wherein the contaminating species is selected from chemical, biological, nuclear or radioactive contaminating species.

17. The method according to claim 16, wherein the contaminating species is a biological species.

18. The method according to claim 12, wherein the gel is applied on the surface in an amount from 100 g to 2,000 g of gel per m² of surface.

19. The method according to claim 12, wherein during step b), drying is carried out at a temperature of 1° C. to 50° C., and under relative humidity from 20% to 80%.

20. The method according to claim 12, wherein the gel is maintained on the surface for a duration from 2 to 72 hours.

21. The method according to claim 12, wherein the gel is maintained on the surface until it exhibits a reduction of its visible and ultraviolet absorbance.

22. The method according to claim 12, wherein the dry and solid residue appears as particles with a size from 1 to 10 mm.

23. The method according to claim 12, wherein the dry and solid residue is removed from the solid surface by brushing and/or suction.

24. The method according to claim 12, wherein the described cycle is repeated from 1 to 10 times by using the same gel during all the cycles or by using different gels during one or several cycle(s).

25. The method according to claim 12, wherein during step b), the gel, before total drying, is re-wetted with a solution of the active decontamination agent of the gel of step a) in the solvent of this gel.

26. The decontamination gel according to claim 1, wherein upon being sprayed and thereafter maintained on a surface for 3 to 24 hours such that the decontamination gel dries, the dried decontamination gel exhibits a relative decrease in visible and ultraviolet light absorbance from 30 to 99% compared to the decontamination gel as sprayed.

27. The decontamination gel according to claim 8, wherein the active decontamination agent is a base selected from the group consisting of sodium hydroxide, potassium hydroxide, and mixtures thereof.

28. The decontamination gel according to claim 8, wherein the active decontamination agent is an acid selected from the group consisting of nitric acid, phosphoric acid, hydrochloric acid, sulfuric acid, hydrogenoxalates, and mixtures thereof.

29. The decontamination gel according to claim 8, wherein the active decontamination agent is an oxidizer selected from the group consisting of peroxides, permanganates, persulfates, ozone, hypochlorites, salts of cerium IV, and mixtures thereof.

30. The decontamination gel according to claim 8, wherein the active decontamination agent is a quaternary ammonium salt selected from the group consisting of hexadecylpyridinium salts.

31. The decontamination gel according to claim 10, wherein the non-ionic surfactants are selected from the group consisting of block, sequenced copolymers and ethoxylated fatty acids.

32. The decontamination gel according to claim 31, wherein the block, sequenced copolymers are copolymers of ethylene oxide and propylene oxide.

33. The method according to claim 15, wherein the solid material is a metal or metal alloy selected from the group consisting of stainless steel, painted steels, aluminum and lead.

34. The method according to claim 15, wherein the solid material is a polymer selected from the group consisting of plastic materials and rubbers.

35. The method according to claim 17, wherein the biological species is selected from the group consisting of bacteria, fungi, yeasts, viruses, toxins, spores and protozoa.

36. The method of claim 17, wherein the biological species is a biotoxic species.

37. The method of claim 36, wherein the biological species is a pathogenic spore.

38. The method of claim 37, wherein the pathogenic spore is Bacillus anthracis.

39. The method of claim 36, wherein the biological species is a toxin.

40. The method of claim 39, wherein the toxin is selected from the group consisting of botulinic toxin and ricin.

41. The method of claim 36, wherein the biological species is a bacteria.

42. The method of claim 41, wherein the bacteria is Yersinia pestis bacteria.

43. The method of claim 36, wherein the biological species is a virus.

44. The method of claim 43, wherein the virus is selected from the group consisting of virus of vaccine or virus of haemorrhagic fevers.

45. The method of claim 44, wherein the virus of haemorrhagic fever is of the Ebola- type.

* * * * *